(12) United States Patent
Matsuura et al.

(10) Patent No.: US 8,216,128 B2
(45) Date of Patent: Jul. 10, 2012

(54) MEDICAL SYSTEM WITH A BIOLOGICAL INFORMATION ACQUIRING APPARATUS AND A MANIPULATION INFORMATION ACQUIRING APPARATUS

(75) Inventors: Wataru Matsuura, Sagamihara (JP); Kazuki Honda, Hachioji (JP); Yasuhito Kura, Hachioji (JP); Yuji Sakamoto, Kunitachi (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/914,296

(22) Filed: Oct. 28, 2010

(65) Prior Publication Data

US 2011/0230712 A1    Sep. 22, 2011

Related U.S. Application Data

(63) Continuation of application No. PCT/JP2010/063041, filed on Aug. 2, 2010.

(30) Foreign Application Priority Data

Aug. 7, 2009   (JP) ................................. 2009-185029

(51) Int. Cl.
   *A61B 1/015*   (2006.01)
   *A61B 1/00*    (2006.01)

(52) U.S. Cl. ........ 600/117; 600/103; 600/114; 600/158; 600/159

(58) Field of Classification Search .................. 600/103, 600/114, 117, 118, 158, 159; 604/65, 66, 604/67

See application file for complete search history.

(56) References Cited

U.S. PATENT DOCUMENTS 5,249,579 A * 10/1993 Hobbs et al. .................. 600/458
5,318,557 A    6/1994 Gross
(Continued)

FOREIGN PATENT DOCUMENTS

EP          0651667 A1    1/1994
(Continued)

OTHER PUBLICATIONS

Abstract only of International Publication No. WO 2006/077529 A2 published Jul. 27, 2006.
(Continued)

*Primary Examiner* — John P Leubecker
*Assistant Examiner* — Ronald D Colque
(74) *Attorney, Agent, or Firm* — Scully, Scott, Murphy & Presser, P.C.

(57) ABSTRACT

A medical system includes an endoscope which is a first medical instrument, a gas supply apparatus which is a second medical instrument that supplies a gas to an insertion site at which an insertion portion of the endoscope is inserted, a biological information acquiring apparatus which is a biological information detection section that detects a blood flow rate at the insertion site as a biological information detected value, a manipulation information acquiring apparatus which is a manipulation information detection section that contacts the insertion portion of the endoscope and is combined with a roller that rotates as the insertion portion moves forward or backward to detect an amount of rotation of the roller as manipulation information, and a system control apparatus provided with a control section that outputs an instruction signal for changing an amount of gas supply to the gas supply apparatus according to the detected value detected by the biological information acquiring apparatus and the manipulation information detected by the manipulation information acquiring apparatus.

3 Claims, 12 Drawing Sheets

U.S. PATENT DOCUMENTS

| | | | |
|---|---|---|---|
| 5,957,880 A * | 9/1999 | Igo et al. | 604/6.11 |
| 2004/0081580 A1 * | 4/2004 | Hole et al. | 422/44 |
| 2004/0111011 A1 | 6/2004 | Uchiyama et al. | |
| 2005/0096502 A1 * | 5/2005 | Khalili | 600/106 |
| 2005/0143623 A1 | 6/2005 | Kojima | |
| 2005/0148847 A1 | 7/2005 | Uchiyama et al. | |
| 2005/0222496 A1 | 10/2005 | Sekiguchi | |
| 2005/0222535 A1 * | 10/2005 | Uesugi et al. | 604/26 |
| 2005/0234391 A1 * | 10/2005 | Uesugi et al. | 604/24 |
| 2006/0030751 A1 * | 2/2006 | Uesugi et al. | 600/101 |
| 2006/0129087 A1 * | 6/2006 | Uesugi et al. | 604/26 |
| 2007/0173689 A1 * | 7/2007 | Ozaki et al. | 600/111 |
| 2007/0244363 A1 * | 10/2007 | Sano et al. | 600/158 |
| 2008/0242931 A1 | 10/2008 | Nishino | |
| 2008/0243146 A1 * | 10/2008 | Sloan et al. | 606/144 |
| 2010/0106080 A1 * | 4/2010 | Uesugi et al. | 604/26 |

FOREIGN PATENT DOCUMENTS

| | | |
|---|---|---|
| EP | 1 582 141 A1 | 10/2005 |
| EP | 1 669 052 A1 | 6/2006 |
| EP | 1 698 267 A1 | 9/2006 |
| EP | 1 825 802 A1 | 8/2007 |
| JP | 8-503384 | 4/1996 |
| JP | 2004-041709 | 2/2004 |
| JP | 2005-102851 | 4/2005 |
| JP | 2005-185452 | 7/2005 |
| JP | 2005-185567 | 7/2005 |
| JP | 2005-312903 | 11/2005 |
| JP | 2005-334331 | 12/2005 |
| JP | 3772157 | 2/2006 |
| JP | 2006-167122 | 6/2006 |
| JP | 2006-263167 | 10/2006 |
| JP | 2006-288822 | 10/2006 |
| JP | 2007-075283 | 3/2007 |
| JP | 2007-075518 | 3/2007 |
| JP | 2007-209750 | 8/2007 |
| JP | 2007-289541 | 11/2007 |
| JP | 2008-532568 A | 8/2008 |
| JP | 2008-534028 A | 8/2008 |
| JP | 2008-237639 | 10/2008 |
| JP | 2009-034367 | 2/2009 |
| WO | WO 2006/064713 A1 | 6/2006 |
| WO | WO 2007/074442 A2 | 7/2007 |

OTHER PUBLICATIONS

Abstract only of International Publication No. WO 2006/077528 A2 published Jul. 27, 2006.

Supplementary European Search Report from corresponding European Patent Application No. EP 10 80 6427.0 dated Jan. 12, 2012.

Abstract of Japanese Patent Publication, No. 2003-339629, dated Dec. 2, 2003.

International Search Report dated Aug. 31, 2010.

* cited by examiner

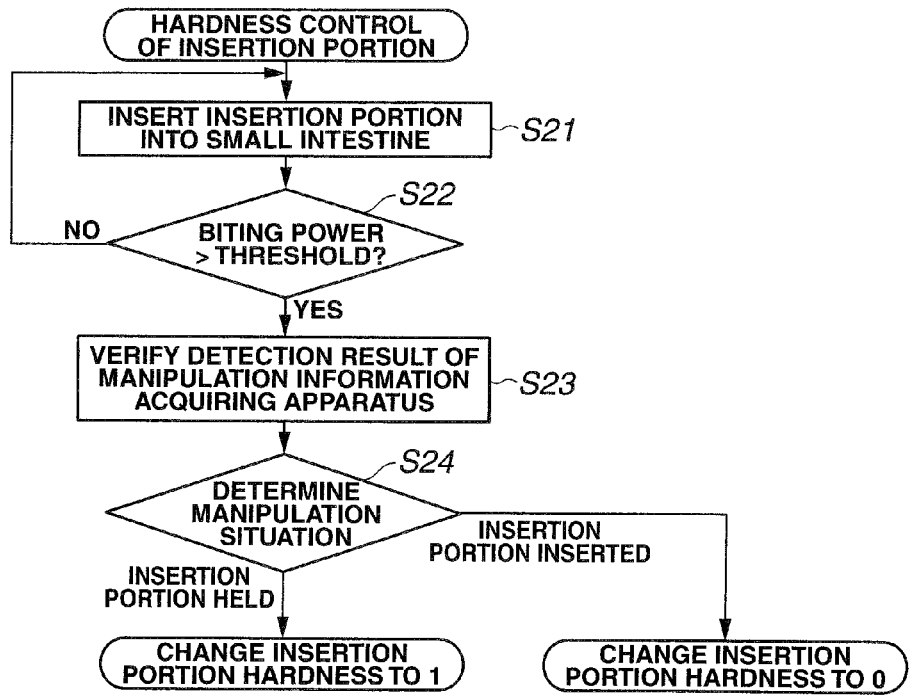
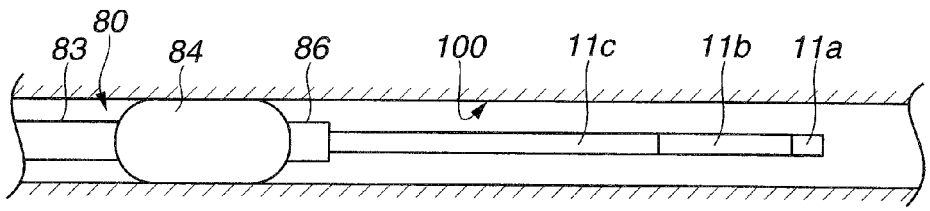
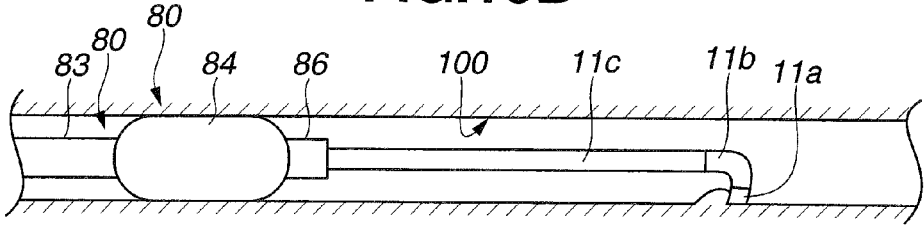
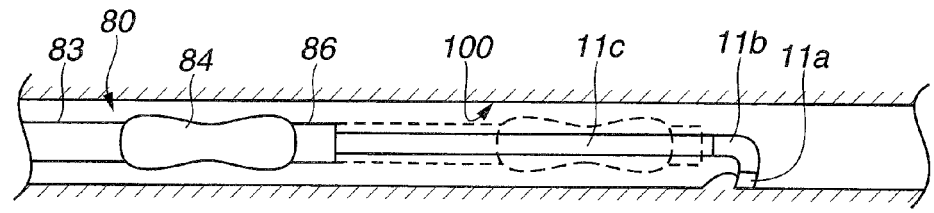

MEDICAL SYSTEM WITH A BIOLOGICAL INFORMATION ACQUIRING APPARATUS AND A MANIPULATION INFORMATION ACQUIRING APPARATUS

CROSS REFERENCE TO RELATED APPLICATION

This application is a continuation application of PCT/JP2010/063041 filed on Aug. 2, 2010 and claims benefit of Japanese Application No. 2009-185029 filed in Japan on Aug. 7, 2009, the entire contents of which are incorporated herein by this reference.

BACKGROUND OF THE INVENTION

1. Field of the Invention

The present invention relates to a medical system equipped with a medical instrument operated by an operator when performing an inspection or medical treatment on a patient, an auxiliary device of the medical instrument and a biological information acquiring apparatus that acquires biological information of the patient under inspection or medical treatment.

2. Description of the Related Art

In recent years, endoscopes are widely used in the medical field. An endoscope is equipped with an elongated insertion portion and an observation can be made by inserting the insertion portion into the body. Furthermore, by introducing a treatment instrument into the body via a treatment instrument channel provided at an insertion portion of the endoscope, it is also possible to perform various types of inspections, medical treatments and procedures.

For example, when the insertion portion of the endoscope is inserted into the depth of an intricate tubular body cavity such as large intestine, the operator operates, for example, a bending knob to cause the bending portion to bend and cause the insertion portion to twist and inserts the distal end portion of the insertion portion into a target region. However, it takes a skill to insert the insertion portion up to the depth of the large intestine smoothly and in a short time without causing any pain to the patient. A skilled operator performs manipulation by empirically deciding a manipulation situation from the condition of the patient and the condition of the operator himself/herself.

Furthermore, a medical system in recent years is configured by including an endoscope, a light source device, a camera controller equipped with an image processing circuit to display an endoscope image, a monitor to display the endoscope image, and moreover, a gas supply apparatus and a high frequency cauterization apparatus. The light source device, the camera controller, the monitor, the air supply apparatus and the high frequency cauterization apparatus are auxiliary apparatuses of the endoscope.

The gas supply apparatus is used to expand the tubular body cavity and improve insertability when the insertion portion of the endoscope is inserted into, for example, the large intestine. The light source device is used to illuminate the inside of the body in endoscope observation. In recent years, light source devices are provided with a narrow band light observation mode that allows a cancer to be identified in addition to a normal-light observation mode for making an ordinary observation. High frequency cauterization apparatuses are used for endoscopic excision of a mucous membrane in which only a mucous membrane containing cancer cells or the like is to be excised.

Japanese Patent Application Laid-Open Publication No. 2005-185452 (hereinafter described as "Document 1") proposes an endoscope apparatus that can prevent unnecessary degradation of a light source of excitation light without requiring any complicated operation. This endoscope apparatus detects a user's endoscope holding state and controls the lighting of the light source lamp according to the detection result. To be more specific, it is disclosed that the endoscope is equipped with a shake sensor that detects the user's holding state, an infrared sensor, a temperature sensor and a pressure sensor or the like, determines the operation situation from the detection result of the sensor, controls ON/OFF of the light source lamp and causes the light source to emit light only in the holding state.

Furthermore, Japanese Patent Application Laid-Open Publication No. 2007-289541 (hereinafter described as "Document 2") proposes an ultrasound medical treatment apparatus that radiates medical treatment ultrasound at an appropriate position even when living tissue such as a blood vessel moves during ultrasound medical treatment and thereby improves the efficiency and stability of ultrasound medical treatment. It is disclosed that this medical treatment apparatus measures the blood flow rate of a lesion, which is a region to be irradiated, and automatically sets the irradiation condition and position of the ultrasound medical treatment device or determines an end of irradiation, according to the rate of change of the measured value.

That is, according to Document 1, operation information of a medical instrument operated by an operator is detected and an auxiliary device for assisting the operator's operation is controlled based on the detection result. On the other hand, according to Document 2, biological information of a patient is detected, and an irradiation condition, an irradiation position or an end of irradiation of a medical instrument is determined based on the detection result.

SUMMARY OF THE INVENTION

A medical system according to an aspect of the present invention is equipped with an endoscope which is a first medical instrument, a gas supply apparatus which is a second medical instrument that supplies a gas to an insertion site at which an insertion portion of the endoscope is inserted, a biological information acquiring apparatus which is a biological information detection section that detects a blood flow rate at the insertion site as a biological information detected value, a manipulation information acquiring apparatus which is a manipulation information detection section that contacts the insertion portion of the endoscope and is combined with a roller that rotates as the insertion portion moves forward or backward to detect an amount of rotation of the roller as manipulation information, and a system control apparatus provided with a control section that outputs an instruction signal for changing an amount of gas supply to the gas supply apparatus according to the detected value detected by the biological information acquiring apparatus and the manipulation information detected by the manipulation information acquiring apparatus.

A medical system according to another aspect of the present invention is equipped with an endoscope which is a first medical instrument, a processor as a second medical instrument that generates an observed image by the endoscope and adjusts a generated image according to a change of an observation mode of a light source device, a biological information acquiring apparatus which is a biological information detection section that detects a pH value in a tubular body cavity into which the endoscope is inserted as a biological information detected value, a manipulation information acquiring apparatus which is a manipulation information detection section that detects an insertion direction and stoppage of the endoscope as manipulation information, and a system control apparatus provided with a control section that determines to change the observation mode of the light source device and outputs an instruction signal to the processor according to the detected value detected by the biological information acquiring apparatus and the manipulation information detected by the manipulation information acquiring apparatus.

A medical system according to a further aspect of the present invention is equipped with an endoscope which is a first medical instrument, a hardness changing apparatus provided in the endoscope which is a second medical instrument that changes hardness of an insertion portion of the endoscope, an over tube through which the insertion portion of the endoscope is inserted and which is provided with a balloon expandable by a fluid supply at an outer circumferential portion, a biological information acquiring apparatus which is a biological information detection section that is provided in a mouth piece worn by a patient, into the body of whom the insertion portion of the endoscope is inserted, and detects an amount of force applied to the mouth piece as a biological information detected value, a manipulation information acquiring apparatus which is a manipulation information detection section that detects a pressure in a balloon provided at the over tube as manipulation information, and a system control apparatus provided with a control section that outputs an instruction signal for changing hardness of the hardness changing apparatus according to the detected value detected by the biological information acquiring apparatus and the manipulation information detected by the manipulation information acquiring apparatus.

A medical system according to a still further aspect of the present invention is equipped with an endoscope which is a first medical instrument, a treatment instrument insertion portion electrically-driven operation forward/backward moving apparatus which is a second medical instrument that drives a treatment instrument inserted into a treatment instrument channel provided in an insertion portion of the endoscope to move forward or backward, a treatment instrument driven to move forward or backward by the treatment instrument insertion portion electrically-driven operation forward/backward moving apparatus, provided with a biological information acquiring apparatus which is a biological information detection section to detect a pH value in the body as a biological information detected value, a manipulation information acquiring apparatus which is a manipulation information detection section that detects the number of times a bending knob for bending a bending portion of the endoscope is operated as manipulation information, and a system control apparatus provided with a control section that outputs an instruction signal that changes a forward/backward moving speed of the treatment instrument by the treatment instrument insertion portion electrically-driven operation forward/backward moving apparatus according to the detected value detected by the biological information acquiring apparatus and the manipulation information detected by the manipulation information acquiring apparatus.

A medical system according to a still further aspect of the present invention is equipped with a capsule endoscope which is a first medical instrument including an image pickup section, a reservoir that stores drug, a drug release section that releases the drug stored in the reservoir, a control section that operates the drug release section, a power supply section that supplies power to the image pickup section, the control section and the drug release section and a drive magnet, a capsule endoscope control system which is a second medical instrument including a manipulation information acquiring apparatus which is a manipulation information detection section that detects a movement status of the capsule endoscope, a guiding magnetism generation section that generates magnetism to guide the capsule endoscope, a power supply, an extracorporeal apparatus that receives a signal transmitted from the capsule endoscope and transmits a signal to the capsule endoscope, an operation section to which an operator's operation instruction is inputted, a display section that can display an image picked up by the capsule endoscope, and a system control section provided with a magnetic field control section and an instruction information determining section, a biological information acquiring apparatus which is a biological information detection section that detects a biological information detected value of a patient into whom the capsule endoscope is inserted and a system control apparatus that outputs an instruction signal for setting an amount of drug sprayed in the system control section according to the detected value detected by the biological information acquiring apparatus and the manipulation information detected by the manipulation information acquiring apparatus.

BRIEF DESCRIPTION OF THE DRAWINGS

FIG. 2 is a diagram illustrating a configuration of a first medical system;

FIG. 3 is a longitudinal cross-sectional view of an anus mount tool;

FIG. 4 is a cross-sectional view along a line IV-IV in FIG. 3;

FIG. 5 is a flowchart illustrating gas supply control in the first medical system;

FIG. 6 is a diagram illustrating a configuration of a second medical system;

FIG. 7 is a flowchart illustrating observation mode control in the second medical system;

FIG. 8 to FIG. 10C are related to a third embodiment of a medical system; FIG. 8 is a diagram illustrating a configuration of a third medical system;

FIG. 9 is a flowchart illustrating balloon control and insertion portion hardness control in the third medical system;

FIG. 10A is a diagram illustrating a situation in which the insertion portion of the endoscope is inserted ahead of the over tube when a balloon is swollen and the over tube is held in a tubular body cavity;

FIG. 10B is a diagram illustrating a situation in which the bending portion of the insertion portion protruding out of the over tube held in the tubular body cavity is bent and the distal end portion is hooked on the tubular body cavity;

FIG. 10C is a diagram illustrating a situation in which the balloon is contracted while the distal end portion is kept hooked on the tubular body cavity wall and the over tube is moved forward;

FIG. 11 is a diagram illustrating a configuration of a fourth medical system;

FIG. 12 is a flowchart illustrating operation of the fourth medical system;

FIG. 13 is a diagram illustrating a configuration of a fifth medical system; and FIG. 14 is a flowchart illustrating operation of the fifth medical system.

DETAILED DESCRIPTION OF THE PREFERRED EMBODIMENTS

Hereinafter, embodiments of the present invention will be described with reference to the accompanying drawings.

Figure 1:
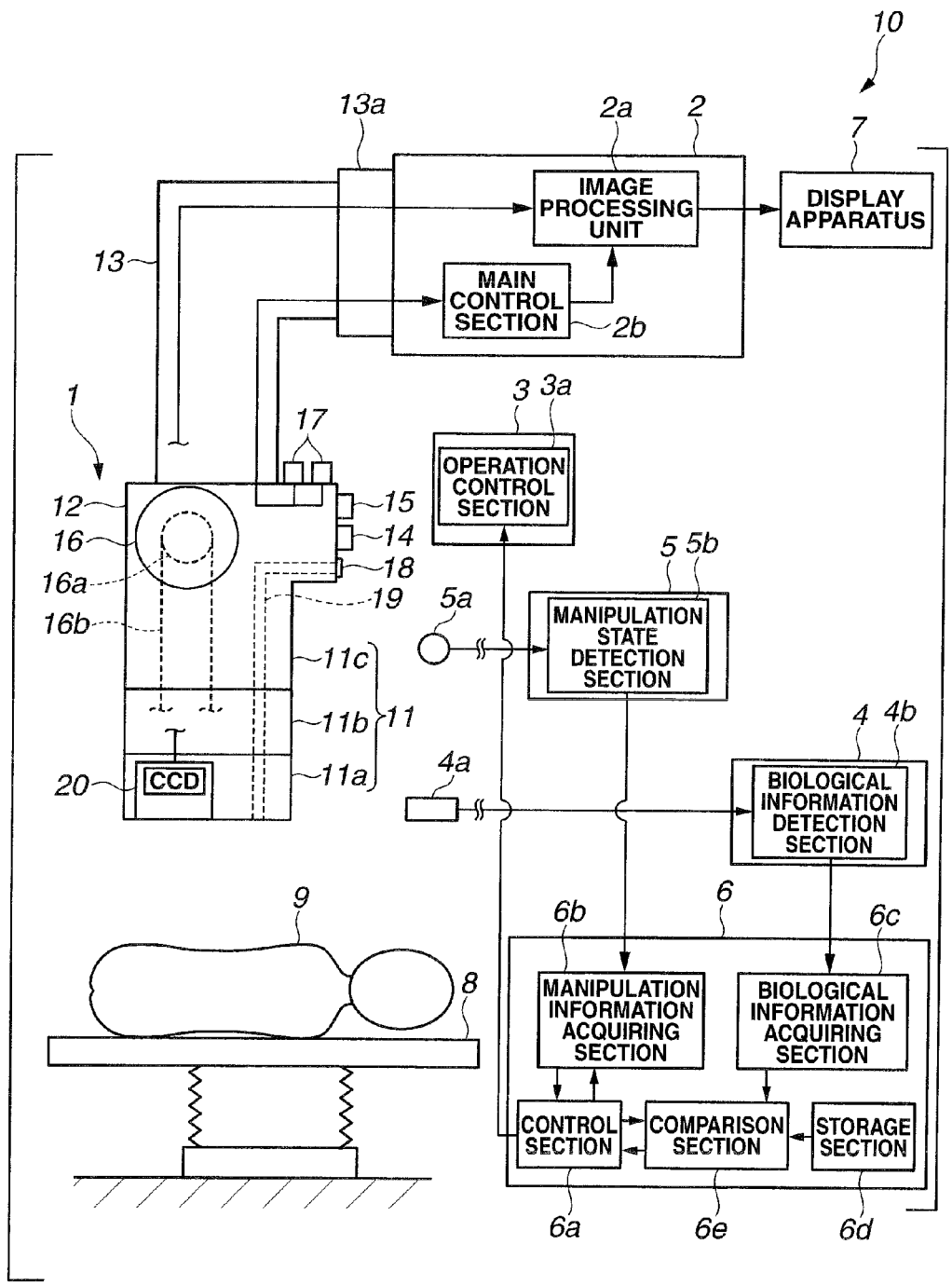
FIG. 1 is a diagram illustrating a schematic configuration of a medical system.

As shown in FIG. 1, a medical system 10 of the present embodiment is configured by including an endoscope 1, a processor 2, an auxiliary device 3, a biological information acquiring apparatus 4, a manipulation information acquiring apparatus 5 and a system control apparatus 6. The endoscope 1 is a first medical instrument operated by the operator. The auxiliary device 3 is a second medical instrument that assists operation of the endoscope 1. The biological information acquiring apparatus 4 is a biological information detection section that acquires biological information of a patient as a biological information detected value. The manipulation information acquiring apparatus 5 is a manipulation information detection section that detects operation of the endoscope 1 and obtains a manipulation situation such as the progress of manipulation as manipulation information. The system control apparatus 6 includes a control section 6a that outputs an instruction signal according to the manipulation information acquired by the manipulation information acquiring apparatus 5 and controls the auxiliary device 3.

Reference numeral 7 denotes a display apparatus and an endoscope image captured by the endoscope 1 is displayed on the display apparatus 7. Reference numeral 8 denotes a bed and a patient 9 lies on the bed 8. The medical system 10 is provided with a light source device (not shown) that illuminates an observation region.

The endoscope 1 is an electronic endoscope including an image pickup apparatus 20 configured by including an image pickup device such as CCD. The endoscope 1 is configured by including an insertion portion 11, an operation section 12 and a universal cord 13. The operation section 12 also functions as a grasping portion and is provided on the proximal end side of the insertion portion 11. The universal cord 13 extends from the operation section 12 and a connector 13a at a proximal end thereof is detachably connected to the processor 2.

The insertion portion 11 is configured by connecting, for example, a rigid distal end portion 11a, a bendable bending portion 11b and a flexible tube section 11c in that order from the distal end side. The operation section 12 is provided with a gas supply/water supply button 14, a suction button 15, a bending knob 16 and various image switches 17. The bending knob 16 is intended to bend the bending portion 11b. The bending portion 11b is configured to perform bending operation when a pulley 16a united with the knob 16 rotates as the bending knob 16 rotates and a bending wire 16b is pulled or relaxed. The image switches 17 output instruction signals for control such as stopping an endoscope image picked up by the image pickup apparatus 20 incorporated in the distal end portion 11a and displayed on a screen of the display apparatus 6.

The endoscope 1 includes a treatment instrument channel 19 that connects a treatment instrument lead out port (not shown) formed in the distal end portion 11a and a treatment instrument insertion port 18 of the operation section 12. The treatment instrument channel 19 is an introduction channel to introduce the treatment instrument into the body cavity. Treatment instruments such as biopsy forceps and electric scalpel are designed to be introduced into the body via the treatment instrument channel 19.

The treatment instrument channel 19 also functions as a suction tube. Furthermore, the insertion portion 11 is provided with a gas supply channel, water supply channel or the like in addition to the treatment instrument channel 19.

The processor 2 is configured by mainly including an image processing unit 2a and a main control section 2b. The image processing unit 2a applies processing such as noise removal processing, A/D conversion processing, image generation processing and D/A conversion processing to an image pickup signal inputted based on the control of the main control section 2b, thereby generates a video signal and outputs the video signal to the display apparatus 7. The signals outputted from the image switches 17 are inputted to the main control section 2b so as to perform control corresponding to the signals.

The auxiliary device 3 is a gas supply apparatus that swells the tubular body cavity or a light source device or the like. The light source device has a normal-light observation mode in which a treatment region is irradiated with white color light for observation and a narrow band light observation mode in which narrow band light is emitted to discover a cancer or the like. When the auxiliary device 3 is a gas supply apparatus, the apparatus is provided with an operation control section 3a that controls an amount of gas supply to the patient, while when the auxiliary device 3 is a light source device, the apparatus is provided with an operation control section 3a that controls a rotary filter.

The biological information acquiring apparatus 4 is provided with a sensor section 4a and a biological information detection section 4b to observe the presence/absence of any change in condition of the patient under inspection or treatment. The sensor section 4a is an infrared sensor or pressure sensor or the like.

The manipulation information acquiring apparatus 5 is provided with a sensor section 5a and a manipulation state detection section 5b. The sensor section 5a detects the operation situation of the endoscope 1 as manipulation information. The manipulation information acquiring apparatus 5 is, for example, an insertion portion insertion amount detection apparatus or a bending operation amount detection apparatus. The insertion portion insertion amount detection apparatus is provided with an encoder in the sensor section 5a to detect movement of the insertion portion 11. When provided with a potentiometer in the sensor section 5a, the bending operation amount detection apparatus detects a rotation of the bending knob 16 or a rotation of the pulley 16a and detects a bending operation of the bending portion 11b. When the sensor section 5a is an optical sensor, the bending operation amount detection apparatus detects movement of the bending wire 16b and detects a bending operation of the bending portion 11b.

The system control apparatus 6 acquires the biological information outputted from the biological information acquiring apparatus 4 and the detection result outputted from the manipulation information acquiring apparatus 5 during manipulation and controls the auxiliary device 3 during manipulation. The system control apparatus 6 is provided with the control section 6a, a manipulation information acquiring section 6b, a biological information acquiring section 6c, a storage section 6d and a comparison section 6e.

The detection result detected by the manipulation state detection section 5b of the manipulation information acquiring apparatus 5 is inputted to the manipulation information acquiring section 6b. The biological information detected value detected by the biological information detection section 4b of the biological information acquiring apparatus 4 is inputted to the biological information acquiring section 6c. A threshold which is a reference value to determine whether or not to output an instruction signal from the biological information of the patient is registered with the storage section 6d. The comparison section 6e compares the threshold registered with the storage section 6d with the biological infatuation detected value inputted to the biological information acquiring section 6c. The control section 6a outputs an instruction signal for controlling the operation of the auxiliary device 3 to the operation control section 3a based on the comparison result of the comparison section 6e and the detection result of the manipulation state detection section 5b. That is, when outputting an instruction signal to the operation control section 3a, the control section 6a determines the manipulation situation from the detection result inputted to the manipulation information acquiring section 6b, determines an optimum control value in that manipulation situation and outputs the control value as an instruction signal.

Hereinafter, a specific configuration example of the medical system 10 will be described with reference to the attached drawings.

Figure 2:
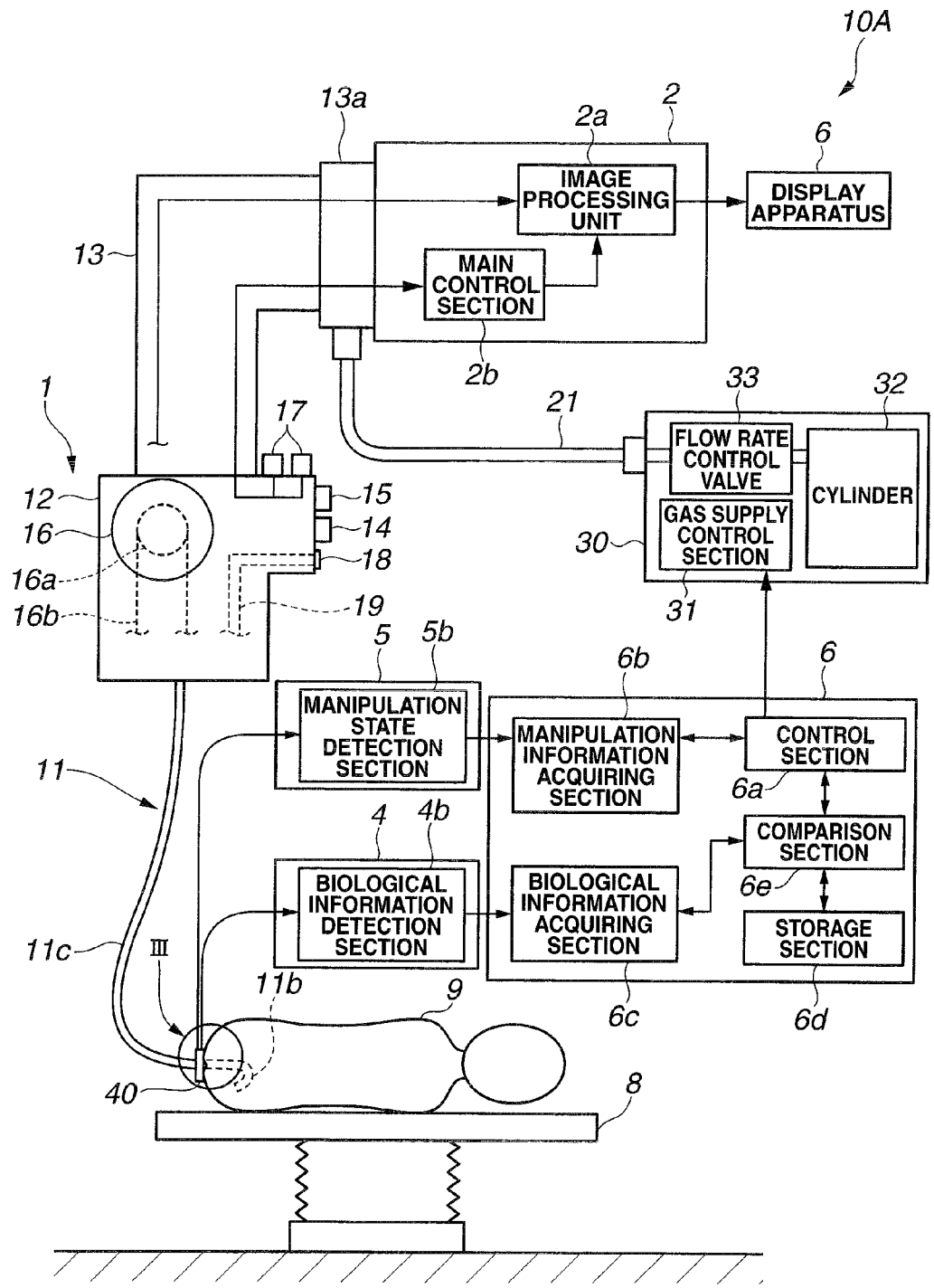
FIG. 2 to FIG. 5 are related to a first embodiment of a medical system.
Figure 3:
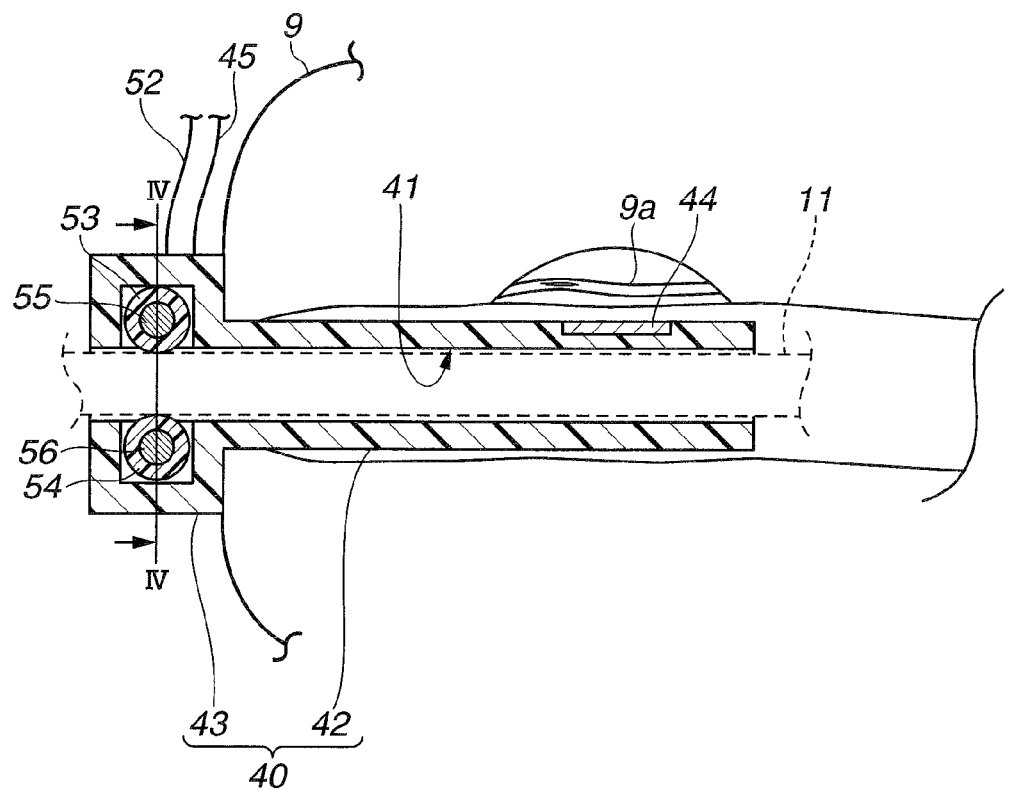
Figure 4:
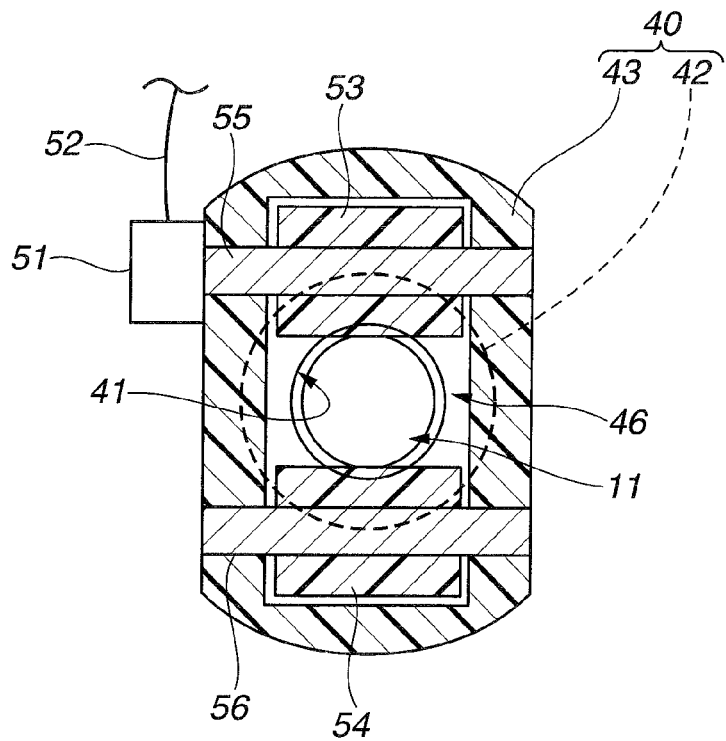
Figure 5:
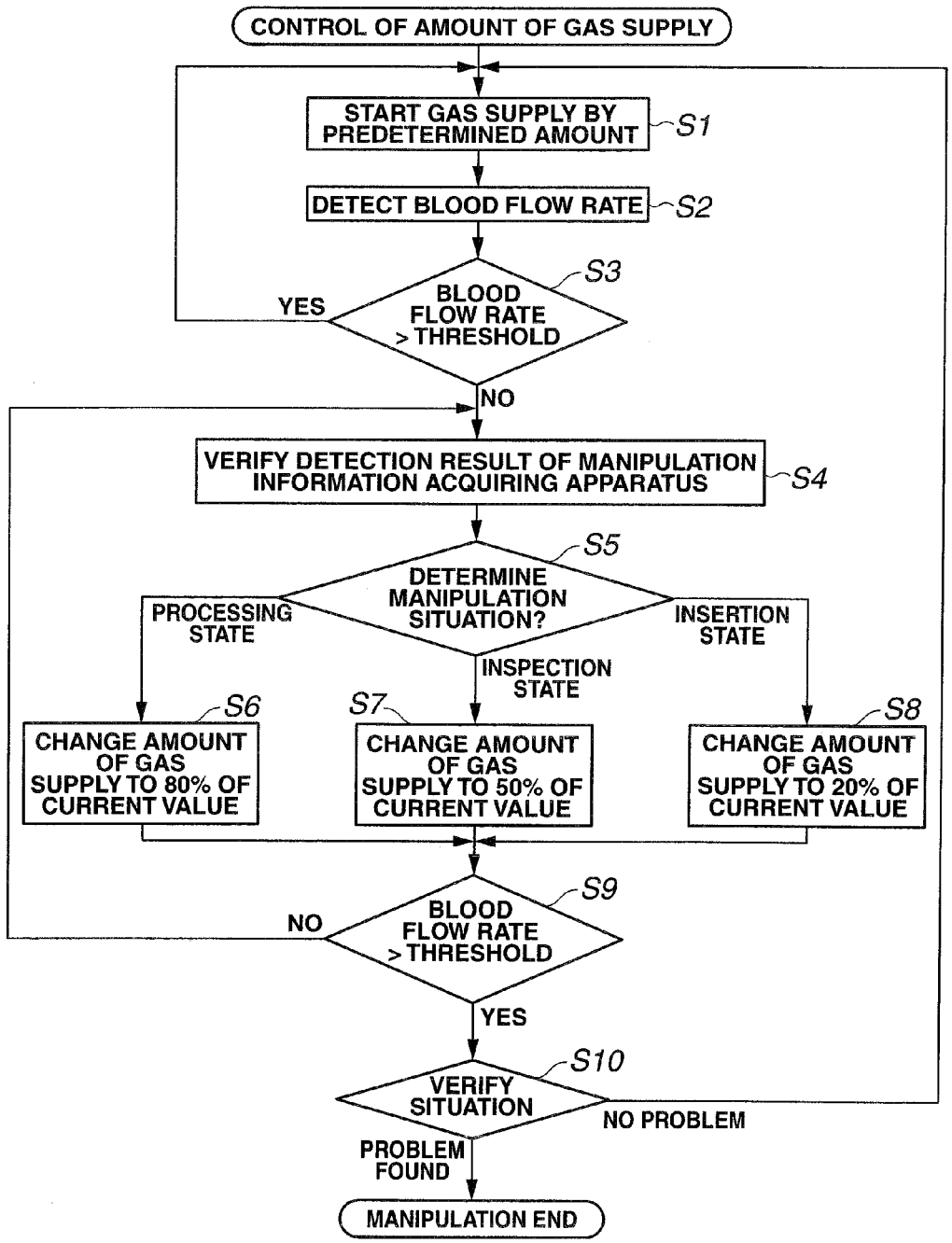

FIG. 2 to FIG. 5 are related to the first embodiment of the medical system, FIG. 2 is a diagram illustrating a configuration of a first medical system, FIG. 3 is a longitudinal cross-sectional view of an anus mount tool shown by an arrow III in FIG. 2, FIG. 4 is a cross-sectional view along a line IV-IV in FIG. 3 and FIG. 5 is a flowchart illustrating gas supply control in the first medical system.

As shown in FIG. 2, the first medical system 10A is configured by including an endoscope 1, a processor 2, a gas supply apparatus 30 as the auxiliary device 3, an anus mount tool 40 and a system control apparatus 6.

In the present embodiment, a control section 6a is configured to output an instruction signal for changing the amount of gas supply to a gas supply control section 31 of the gas supply apparatus 30.

The gas supply apparatus 30 is used to supply, for example, air or carbon dioxide to the large intestine to swell the large intestine and improve insertability of the insertion portion 11. The gas supply apparatus 30 is configured by mainly including the gas supply control section 31, a cylinder 32 and a flow rate control valve 33. The gas supply control section 31 corresponds to the operation control section 3a. The cylinder 32 stores a gas to be supplied to the large intestine. The flow rate control valve 33 adjusts the amount of gas supplied into the body. The gas supply apparatus 30 and the endoscope 1 are connected via a gas supply tube 21.

The anus mount tool 40 has a dual function as a biological information acquiring apparatus 4 and a manipulation information acquiring apparatus 5. The anus mount tool 40 is a guide tube provided with a through hole 41 through which the insertion portion 11 is inserted and is provided with a tube body 42 and a collar portion 43 that defines the amount of insertion of the tube body 42 as shown in FIG. 3.

The tube body 42 is configured of an elastic tubular member such as silicon tube and arranged from the anus of the patient 9 in, for example, the rectum. An infrared sensor 44 is disposed on the end face side of the tube body 42 as the sensor section 4a of the biological information acquiring apparatus 4. A signal line 45 extends from the infrared sensor 44. The infrared sensor 44 is provided on the outer circumferential face side of the tube body 42 to detect a flow rate of blood that flows through a blood vessel 9a of the patient 9. The detected value of the infrared sensor 44 is outputted to a biological information detection section 4b shown in FIG. 2 via the signal line 45. The biological information detection section 4b outputs a biological information detected value indicating the blood flow rate to the biological information acquiring section 6c of the system control apparatus 6.

As shown in FIG. 3 and FIG. 4, the collar portion 43 is provided with an encoder 51 as the sensor section 5a of the manipulation information acquiring apparatus 5. A signal line 52 extends from the encoder 51. The encoder 51 detects forward/backward movement and stoppage of the insertion portion 11 of the endoscope 1. A pair of pivotable rollers 53 and 54 are disposed in an inner space 46 of the collar portion 43.

The two rollers 53 and 54 are each formed of an elastic resin member or rubber member. The rollers 53 and 54 are integrally fixed to rotation shafts 55 and 56. The outer surface of the insertion portion 11 which is inserted into the through hole 41 is pressed and sandwiched by the rollers 53 and 54.

The rotation shafts 55 and 56 are driven shafts. In the present embodiment, for example, rotation of one end of the rotation shaft 55 is designed to be detected by the encoder 51. To be more specific, the encoder 51 detects the rotation direction and rotation speed of the rotation shaft 55. The detected value detected by the encoder 51 is outputted to a manipulation state detection section 5b shown in FIG. 2 via the signal line 52.

The manipulation state detection section 5b outputs manipulation situation data which is manipulation information to a manipulation information acquiring section 6b of the system control apparatus 6. That is, the manipulation state detection section 5b determines, through the encoder 51, whether the rotation shaft 55 rotates clockwise for a large proportion of time within a predetermined time or rotates counterclockwise for a large proportion of time or stops operation rather than it rotates for a large proportion of time, and outputs the detection result indicating that the operation state of the insertion portion 11 is forward movement, backward movement or stoppage to the manipulation information acquiring section 6b.

The gas supply amount control of the gas supply apparatus 30 when large intestine endoscopy is performed using the first medical system 10A configured as described above will be described.

First, when performing the large intestine endoscopy, the operator registers the patient's blood flow rate data with a storage section 6d of the system control apparatus 6 as a threshold. Furthermore, the operator places the anus mount tool 40 at a predetermined position of the anus. Then, detection of the blood flow rate is started.

The control section 6a determines a comparison result of a comparison section 6e. The comparison section 6e compares the blood flow rate detected by the infrared sensor 44 and outputted to a biological information acquiring section 6c with the patient's blood flow rate data registered with the storage section 6d beforehand and determines whether or not any burden is placed on the patient 9.

Upon determining that the blood flow rate is lower than the blood flow rate data although it is immediately after the attachment of the anus mount tool 40 to the anus, the control section 6a stops the subsequent processing. In this case, the control section 6a notifies the operator of abnormality using a buzzer tone.

On the other hand, upon determining that the blood flow rate is higher than the blood flow rate data, the control section 6a determines that no burden is placed on the patient 9 and starts manipulation. That is, the operator arranges the insertion portion 11 between the rollers 53 and 54 and starts insertion manipulation.

That is, as shown in step S1 in FIG. 5, a predetermined amount of, for example, air is supplied from the gas supply apparatus 30 to the endoscope 1. The air is supplied to the large intestine via the gas supply tube and the gas supply channel, causing the large intestine to swell. The operator inserts the insertion portion 11 into the large intestine swollen by the air and continues to insert the insertion portion 11 to the depth.

While the air is being supplied to the large intestine, the biological information acquiring apparatus 4 continues to detect the blood flow rate as shown in step S2. The control section 6a then determines in step S3 that the patient's abdomen or the like is not pressed by the swelling of the large intestine as long as the comparison section 6e determines that the blood flow rate is higher than a threshold. As a result, a predetermined amount of air is continued to be supplied from the gas supply apparatus 30 to the endoscope 1. In the meantime, the operator continues insertion manipulation.

On the other hand, in step S3, upon determining through the comparison section 6e that the blood flow rate is lower than the threshold, the control section 6a suspects that the patient's large intestine might have swollen excessively and moves to step S4. Here, the control section 6a verifies the current manipulation situation and then performs control over the amount of air supply.

That is, in step S4, the control section 6a verifies the detection result inputted from the manipulation information acquiring apparatus 5 to the manipulation information acquiring section 6b first. Next, the control section 6a moves to step S5 and determines the manipulation situation of the endoscope 1 from the verified detection result.

Here, upon verifying that the detection result that the operation of the insertion portion 11 is stopped has been inputted to the manipulation information acquiring section 6b, the control section 6a determines the manipulation situation to be a treatment state and moves to step S6. On the other hand, upon verifying that the detection result that the operation of the insertion portion 11 is backward movement has been inputted to the manipulation information acquiring section 6b, the control section 6a determines the manipulation situation to be an inspection state and moves to step S7. Furthermore, upon verifying that the detection result that the operation of the insertion portion 11 is forward movement has been inputted to the manipulation information acquiring section 6b, the control section 6a determines the manipulation situation to be an insertion state and moves to step S8.

In step S6, the control section 6a outputs an instruction signal indicating that the amount of gas supply is changed to 80% of the current value to the gas supply control section 31 of the gas supply apparatus 30. This causes the amount of gas supply from the gas supply apparatus 30 to the endoscope 1 to slightly reduce and thereby prevents excessive swelling. This control prevents the interior of the large intestine from drastically deforming and allows the operator to continue treatment.

In step S9, when the blood flow rate is not determined to be higher than a threshold, the control section 6a returns to step S4 again. Here, aiming at a reduction of the amount of gas supply, the control section 6a tries to avoid excessive swelling. Upon verifying in step S9 that the blood flow rate is higher than the threshold, the control section 6a moves to step S9 and enters a standby state.

In the standby state, the operator verifies the situation such as the patient's condition and determines whether or not to continue manipulation or the like. Here, when the operator determines that there is no problem with the continuation of manipulation, the control section 6a moves to step S1 and continues the manipulation with a newly set amount of gas supply. On the other hand, in step S10, when the operator verifies the situation of the patient and determines that there is a problem, the manipulation is ended.

On the other hand, in step S7, the control section 6a outputs an instruction signal for changing the amount of gas supply to 50% of the current value to the gas supply control section 31 of the gas supply apparatus 30. This reduces the amount of gas supply from the gas supply apparatus 30 to the endoscope 1 by half, and can thereby prevent excessive swelling. In this case, the operator can smoothly move the insertion portion 11 through the swollen large intestine and speedily move the insertion portion 11 backward.

In step S9, the control section 6a tries to reduce the amount of gas supply and stop excessive swelling until the blood flow rate is determined to be higher than a threshold. In step S9, upon verifying that the blood flow rate is higher than the blood flow rate data, the control section 6a moves to step S10 and enters a standby state.

Furthermore, in step S8, the control section 6a outputs an instruction signal for changing the amount of gas supply to 20% of the current value to the gas supply control section 31 of the gas supply apparatus 30. This drastically reduces the amount of gas supply from the gas supply apparatus 30 to the endoscope 1.

In step S9, the control section 6a tries reducing the amount of gas supply and stop excessive swelling until the blood flow rate is determined to be higher than the threshold. Upon verifying in step S9 that the blood flow rate is higher than the blood flow rate data, the control section 6a moves to step S10 and enters a standby state.

Thus, the control section of the system control apparatus can easily determine whether or not there is a certain possibility that the patient's large intestine may be excessively swollen by the air or the like supplied from the gas supply apparatus, causing damage to the intestinal tract based on the determination result of a comparison by the comparison section between the blood flow rate of the patient and a threshold during manipulation.

When the comparison section determines that the large intestine of the patient is excessively swollen, the control section can determine the manipulation situation and automatically reduce the amount of gas supply according to the manipulation situation.

Thus, in the treatment state, it is possible to prevent excessive swelling while preventing adverse influences on the treatment caused by a drastic change in the swelling state of the large intestine.

Furthermore, in the inspection state, it is possible to prevent excessive swelling while smoothly withdrawing the insertion portion by reducing the amount of gas supply by half.

Furthermore, in the insertion state, by drastically reducing the amount of gas supply and thereby speedily preventing excessive swelling, it is possible to prevent the patient's intestinal tract from being damaged by a gas supply.

Although the aforementioned present embodiment has adopted the infrared sensor 44 as the sensor section 4a of the biological information acquiring apparatus 4, the sensor section is not limited to the infrared sensor but a sensor such as ultrasound sensor may also be used.

Furthermore, the present embodiment has adopted the encoder 51 as the sensor section 5a of the manipulation information acquiring apparatus 5 to detect the moving direction of the insertion portion 11 and the control section 6a determines the manipulation situation. However, the determination of the manipulation situation by the control section 6a is not limited to forward/backward movement or stoppage of the insertion portion, but a configuration of detecting the speed of rotation operation of the bending knob 16 or the like may also be adopted.

In this configuration, when the operation of the bending knob 16 is detected to be performed faster than a threshold, an insertion state or inspection state is determined, while when the operation of the bending knob 16 is detected to be performed more slowly than a threshold, the state is determined to be a treatment state. The detection apparatus that detects the speed of rotation operation may be either detachably provided for the operation section 12 or fixed to the interior or exterior of the operation section 12 beforehand.

Furthermore, in the present embodiment, the anus mount tool 40 has a dual function as the biological information acquiring apparatus 4 and the manipulation information acquiring apparatus 5. However, a configuration may be adopted in which the biological information acquiring apparatus 4 and the manipulation information acquiring apparatus 5 are provided as independent members. That is, such a configuration may be adopted that a tube body provided with the infrared sensor 44 and the insertion portion movement detection apparatus provided with a pair of rollers 53 and 54 are provided as independent members.

Figure 6:
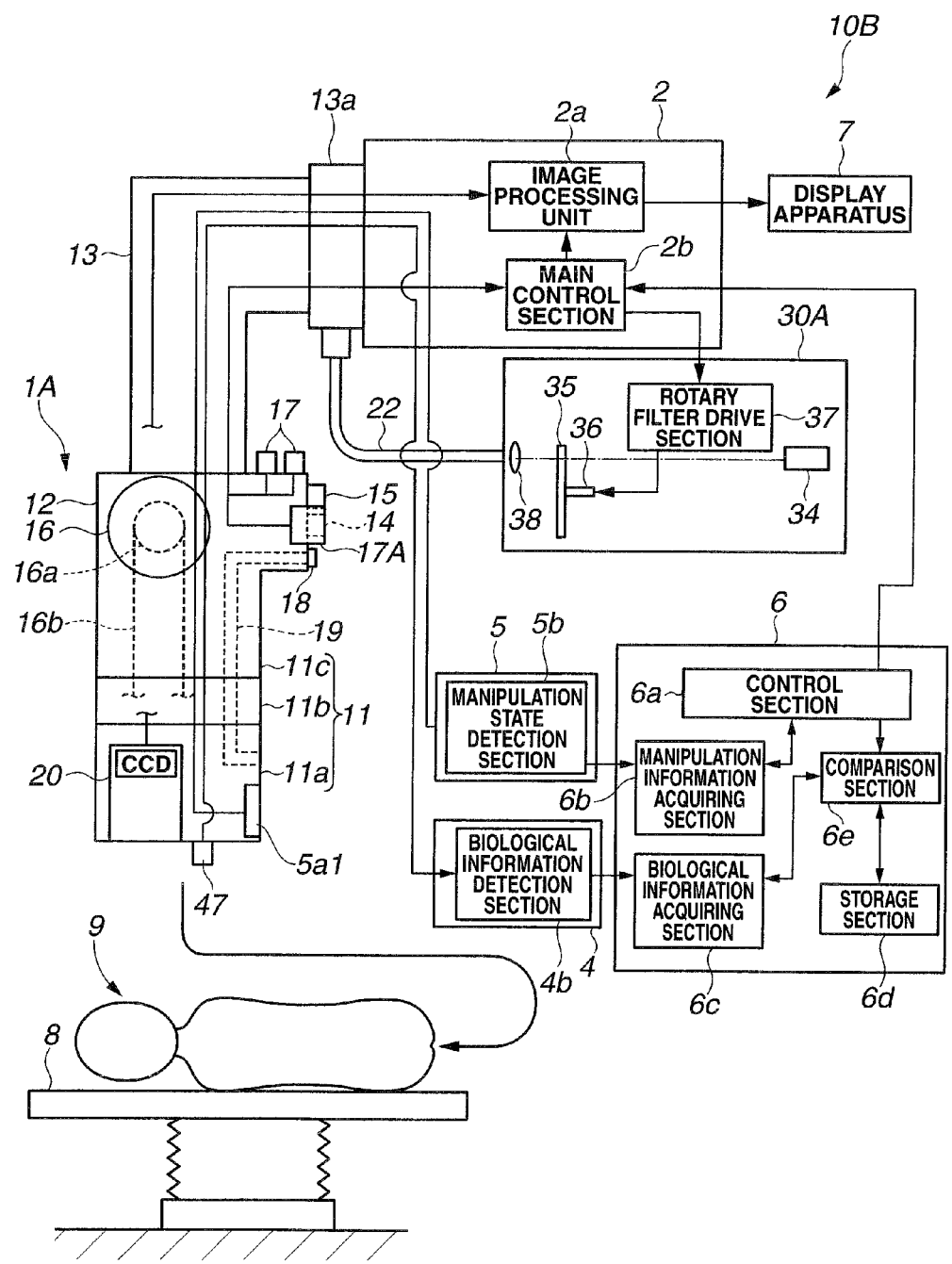
FIG. 6 and FIG. 7 are related to a second embodiment of a medical system.
Figure 7:
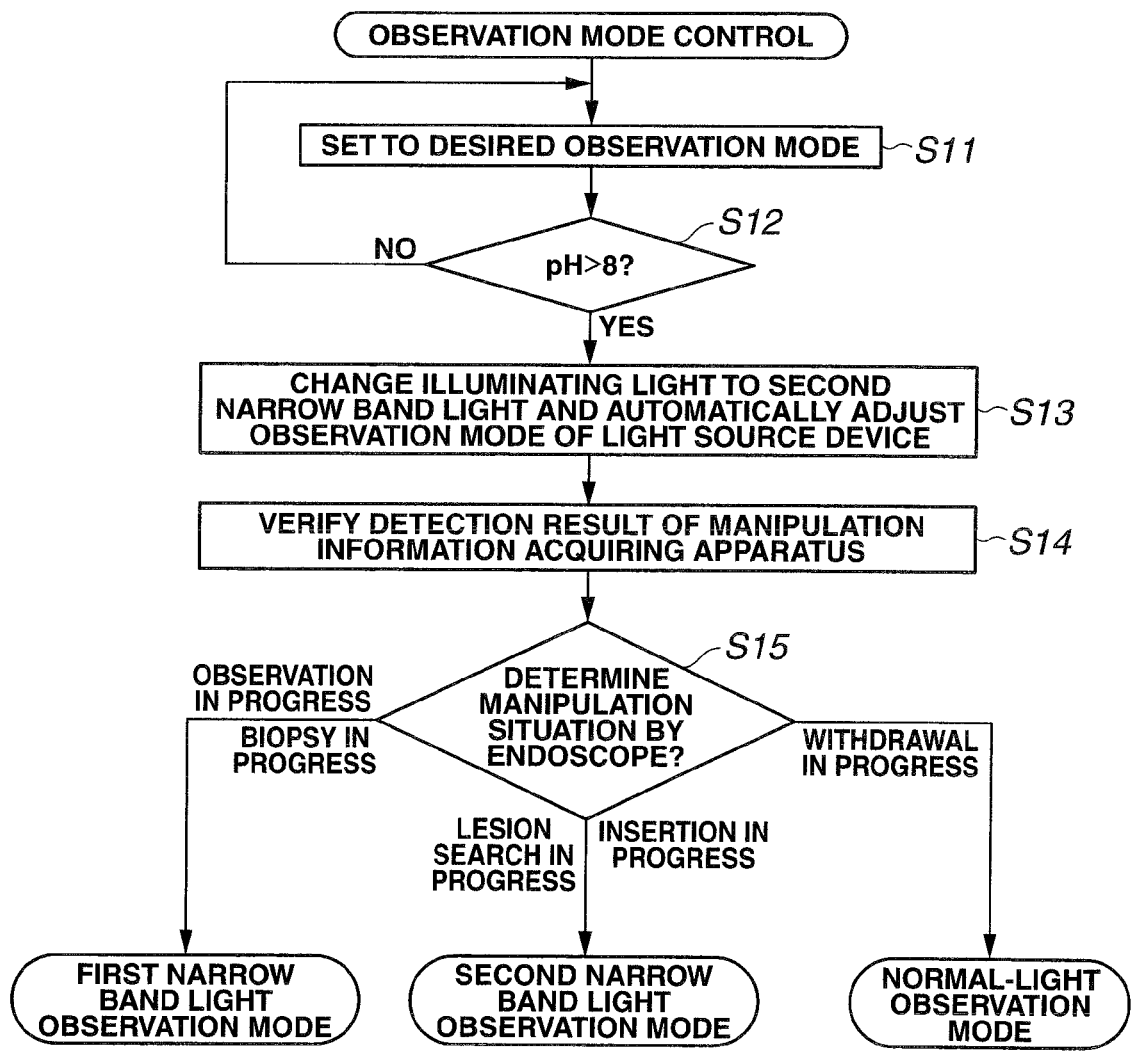

FIG. 6 and FIG. 7 are related to a second embodiment of a medical system, FIG. 6 is a diagram illustrating a configuration of a second medical system and FIG. 7 is a flowchart illustrating observation mode control of illuminating light in the second medical system. In the present embodiment, members similar to those in the first embodiment will be assigned the same reference numerals and descriptions thereof will be omitted.

As shown in FIG. 6, a second medical system 10B is configured by including an endoscope 1A, a processor 2 as the auxiliary device 3, a manipulation information acquiring apparatus 5, a light source device 30A, a pH sensor (hereinafter described as "pH sensor") 47 as the biological information acquiring apparatus 4 and a system control apparatus 6.

The manipulation information acquiring apparatus 5 of the present embodiment is provided with an infrared sensor 5a1 as the sensor section 5a that detects an operation situation of the endoscope 1A. The infrared sensor 5a1 is disposed on the circumferential surface on the distal end portion 11a side of the insertion portion 11 of the endoscope 1A. The infrared sensor 5a1 detects whether the operation state of the insertion portion 11 is forward movement, backward movement or stoppage. A signal line extending from the infrared sensor 5a1 is connected to the manipulation information acquiring apparatus 5 via, for example, the processor 2. The detected value of the sensor 5a1 is outputted to a manipulation state detection section 5b of the manipulation information acquiring apparatus 5 via the signal line. The manipulation state detection section 5b determines whether the operation state of the insertion portion 11 is forward movement, backward movement or stoppage from the detected value outputted from the infrared sensor 5a1 and outputs the detection result of forward movement, backward movement or stoppage to a manipulation information acquiring section 6b of the system control apparatus 6.

In the present embodiment, a control section 6a is configured to output an instruction signal for changing an observation mode to a main control section 2b of the processor 2.

The endoscope 1A is provided with a mode changeover switch 17A. When the mode changeover switch 17A is operated, the light source device 30A is enabled to change the observation mode of illuminating light outputted from the light source device 30A.

The light source device 30A includes a white color light source 34, a rotary filter 35, a motor 36, a rotary filter drive section 37 and a condensing optical system 38. The white color light source 34 is a lamp such as xenon lamp. The rotary filter 35 transforms white color light emitted from the white color light source 34 into frame sequential illuminating light. The motor 36 drives the rotary filter 35 to rotate. The rotary filter drive section 37 drives the motor 36 based on the control from the main control section 2b. The condensing optical system 38 condenses the illuminating light that has passed through the rotary filter 35 and supplies the illuminating light to the incident end face of a light guide fiber 22.

The light source device 30A is provided with not only a normal-light observation mode in which white light is radiated onto a subject in a living body and it is possible to obtain an image of the subject substantially identical to that observed by naked eye but also a narrow band light observation mode. The "narrow band light observation mode" is an observation mode in which an observation is realized by radiating narrow band light which is light having a band narrower than illuminating light in the normal-light observation mode onto the subject to make it possible to obtain images of the blood vessel of the mucous membrane surface layer or the like in the living body more emphasized than in the normal observation.

The light source device 30A and the endoscope 1A are connected via the light guide fiber 22.

The rotary filter 35 is configured into a disk shape, rotates around its shaft as the center and configured by including a first filter group provided with a plurality of filters and a second filter group provided with a plurality of filters. The first filter group is configured by including an R filter that allows to pass light of a red color wavelength band, a G filter that allows to pass light of a green color wavelength band and a B filter that allows to pass light of a blue color wavelength band. White color light emitted from the white color light source 34 passes through the first filter group and is thereby transformed to wideband light for a normal-light observation mode.

The second filter group is configured by including a Bn filter that allows to pass light of a blue color and narrow band and a Gn filter that allows to pass light of a green color and narrow band. The Bn filter allows to pass narrow band light (Bn light) on the short wavelength side of blue light and the Gn filter is configured to allow to pass narrow band light (Gn light) having a center wavelength of, for example, approximately 540 nm. That is, the white color light emitted from the white color light source 34 is discretized through the second filter group and thereby transformed into narrow band light with a plurality of bands for a narrow band light observation mode.

When the light source device 30A is in a normal-light observation mode or a plurality of narrow band light observation modes, the image processing unit 2a of the processor 2 applies predetermined processing to a video signal based on the control of the main control section 2b, generates video signals corresponding to the respective observation modes and outputs the video signals to the display apparatus 7.

The pH sensor 47 is disposed at the distal end portion 11a of the insertion portion 11 and is configured to protrude by a predetermined amount. A signal line extending from the pH sensor 47 is outputted to a biological information detection section 4b via, for example, the processor 2. The biological information detection section 4b outputs a pH value to a biological information acquiring section 6c of the system control apparatus 6 as a biological information detected value.

Observation mode control when conducting endoscopy for inspecting the presence/absence of, for example, a cancer or performing treatment of a cancer using an endoscope using the second medical system 10B configured as described above will be described.

When performing inspection or treatment using the endoscope, the operator registers a pH value of the bile of the patient, for example, pH8 as a threshold with a storage section 6d of the system control apparatus 6. Furthermore, the operator prepares the light source device 30A that can make an observation in the narrow band light observation mode in addition to the normal-light observation mode.

The light source device 30A of the present embodiment is configured to be able to switch between a normal-light observation mode, a first narrow band light observation mode which is a narrow band light observation state and gives priority to identification of a cancer and a second narrow band light observation mode which allows a cancer to be identified while preventing the bile from being mistaken for hemorrhage according to an instruction signal inputted to the main control section 2b.

That is, the order of ease of identification of a cancer in different observation modes is: first narrow band light observation mode>second narrow band light observation mode>normal-light observation mode.

Next, the operator starts inspection or treatment. That is, the operator inserts the insertion portion 11 into the body through, for example, the anus, operates the mode changeover switch 17A as shown in step S11 in FIG. 7 and sets the observation mode to a desired observation mode. The operator then starts to insert the insertion portion 11 into the body. When inspecting the presence/absence of a cancer, the operator operates the mode changeover switch 17A to set the observation mode of the light source device 30A to a first narrow band light observation mode.

In step S12, the control section 6a verifies the comparison result of a comparison section 6e. That is, the control section 6a verifies whether or not the pH value inputted to the biological information acquiring section 6c exceeds a threshold (pH8) registered with the storage section 6d.

Upon verifying that the inputted pH value is equal to or below pH8, the control section 6a moves to step S11. The operator operates the mode changeover switch 17A as appropriate, changes the observation mode to a desired observation mode and continues to move the insertion portion 11 to a target region.

On the other hand, upon verifying that the pH value determined by the comparison section 6e is equal to or above pH8 in step S12, the control section 6a moves to step S13 and then to step S14.

First, in step S13, the control section 6a outputs an instruction signal for changing illuminating light to the second narrow band light to the main control section 2b of the processor 2 and notifies the operator that bile has been detected and that observation light will be changed automatically on, for example, a screen of the display apparatus 7. In this case, characters such as "observation mode will be changed automatically" are displayed on the display apparatus 7.

When an image including the bile is displayed on the screen of the display apparatus 7, this prevents the bile from being displayed with the same red color as the color of blood, and can thereby prevent the operator from mistaking the bile for hemorrhage.

Next, in step S14, the control section 6a verifies the detection result inputted from the manipulation information acquiring apparatus 5 to the manipulation information acquiring section 6b. Next, the control section 6a moves to step S15 and determines the manipulation situation by the endoscope 1A from the verified detection result.

Upon verifying that a detection result of forward movement has been inputted to the manipulation information acquiring section 6b, the control section 6a determines that the manipulation situation of the endoscope is insertion in progress or search for a lesion in progress, and outputs an instruction signal for maintaining second narrow band light. The observation mode of the light source device 30A is thereby automatically kept to the second narrow band light observation mode.

On the other hand, in step S15 upon detecting that a detection result of stoppage has been inputted to the manipulation information acquiring section 6b, the control section 6a determines that observation is in progress or biopsy is in progress, and outputs an instruction signal for changing the illuminating light to the first narrow band light to the main control section 2b of the processor 2. Thus, the observation mode of the light source device 30A is automatically changed from the second narrow band light observation mode to the first narrow band light observation mode in which first narrow band light is emitted. An image with the highest priority given to visualization of the lesion is displayed on the screen of the display apparatus 7.

Furthermore, in step S15, upon verifying that a detection result of backward movement has been inputted to the manipulation information acquiring section 6b, the control section 6a determines that the insertion portion is being withdrawn and outputs an instruction signal for changing the illuminating light to normal light to the main control section 2b of the processor 2. Thus, the observation mode of the light source device 30A is automatically changed from the second narrow band light observation mode to the normal-light observation mode. A normal observed image is displayed on the screen of the display apparatus 7 and it is thereby possible to withdraw the insertion portion without mistaking the bile for hemorrhage even when an image of the bile appears.

Thus, the control section of the system control apparatus verifies the presence/absence of the bile using the pH sensor provided at the distal end of the insertion portion and verifies the operation situation of the insertion portion from the detection result of the infrared sensor. Upon verifying the bile through the pH sensor, the control section speedily changes the observation mode of the light source device to the second narrow band light observation mode. This prevents the operator from mistaking the bile displayed on the screen for hemorrhage.

The control section changes the observation mode of the light source device to the second narrow band light observation mode and then determines that the manipulation situation of the endoscope is observation in progress, biopsy in progress, insertion in progress, lesion search in progress or insertion portion being withdrawn, from the operation state of the insertion portion and automatically changes the observation mode of the light source device.

Since the observation mode of the light source device is automatically changed, after detecting the bile, the operator can perform observation/biopsy with the highest priority given to visualization of the lesion by placing the insertion portion in a stopped state, continue insertion or perform a lesion search while visualizing the lesion by moving the insertion portion forward without mistaking the bile for hemorrhage or withdraw the insertion portion by moving the insertion portion backward without mistaking the bile for hemorrhage.

Figure 8:
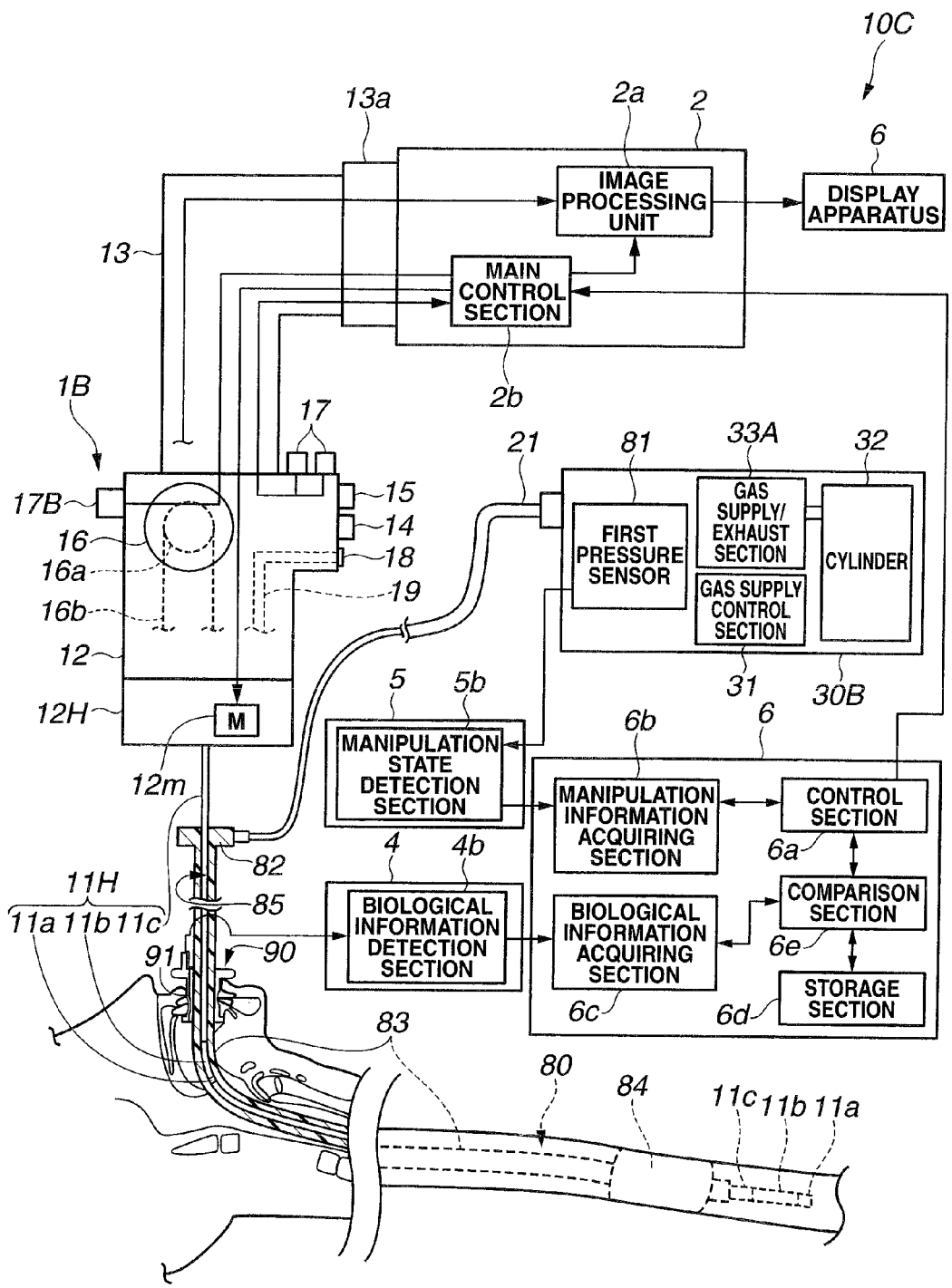

FIG. 8 to FIG. 10C are related to a third embodiment of a medical system, FIG. 8 is a diagram illustrating a configuration of a third medical system, FIG. 9 is a flowchart illustrating balloon control and insertion portion hardness control in the third medical system, FIG. 10A is a diagram illustrating a situation in which the insertion portion of the endoscope is inserted ahead of the over tube when a balloon is swollen and the over tube is held in a tubular body cavity, FIG. 10B is a diagram illustrating a situation in which the bending portion of the insertion portion protruding out of the over tube held in the tubular body cavity is bent and the distal end portion is hooked on the tubular body cavity and FIG. 10C is a diagram illustrating a situation in which the balloon is contracted while the distal end portion is kept hooked on the tubular body cavity wall and the over tube is moved forward. In the present embodiment, members similar to those in the aforementioned embodiments will be assigned the same reference numerals and descriptions thereof will be omitted.

As shown in FIG. 8, the third medical system 10C is configured by including an endoscope 1B, an over tube 80, a processor 2, a gas supply apparatus 30B which is a fluid supply apparatus, a mouth piece 90 and a system control apparatus 6.

The endoscope 1B of the present embodiment is provided with a hardness changing apparatus 12H as the auxiliary device 3 that changes hardness of an insertion portion 11H and the hardness changing apparatus 12H is provided with a motor 12m. The insertion portion 11H is inserted into the over tube 80.

The gas supply apparatus 30B is provided with a pressure detection sensor (hereinafter described as "first pressure sensor") 81 as the manipulation information acquiring apparatus 5. The mouth piece 90 is the biological information acquiring apparatus 4 and is provided with a biting power detection pressure sensor (hereinafter described as "second pressure sensor") 91 as the sensor section 4a.

In the present embodiment, the control section 6a is configured to output an instruction signal to a main control section 2b of the processor 2.

The hardness changing apparatus 12H provided for the endoscope 1B of the present embodiment is configured by including a close-contact coil (not shown) in the insertion portion 11H and a wire member (not shown) inserted into the close-contact coil. The hardness changing apparatus 12H is designed to change the hardness of the insertion portion 11H by applying a compression force to the close-contact coil and thereby hardening the close-contact coil by pulling the close-contact coil via the wire member. Such a hardness changing apparatus (also referred to as "variable hardness mechanism") is described in detail, for example, in Japanese Patent No. 3772157.

In the present embodiment, the hardness of the insertion portion 11H is changed through driving of the motor 12m disposed in the hardness changing apparatus 12H of the operation section 12. That is, there is such a configuration that the wire member (not shown) is driven by the motor 12m to move by a predetermined amount so as to be able to change the flexibility level of the insertion portion 11H in three stages of hardness "0", hardness "1" and hardness "2." The insertion portion 11H is most flexible with hardness "0" and most inflexible with hardness "2."

The hardness of the insertion portion 11 can be changed as appropriate by operating a hardness adjustment switch 17B provided in the operation section 12, that is, according to a manual operation thereof. A control signal outputted from the hardness adjustment switch 17B is outputted to the motor 12m via the main control section 2b.

The over tube 80 is made up of a multi-lumen tube and at least has an insertion portion insertion hole 85 through which the insertion portion 11H of the endoscope 1B can be inserted and a gas supply hole (not shown) for gas supply. The over tube 80 is made up of a tube coupling section 82 and a tube body 83, and an over tube balloon (hereinafter abbreviated as "balloon") 84 is disposed at a distal end of the tube body 83.

One opening of the gas supply hole is connected to the inside of the balloon 84 and the other opening of the gas supply hole is connected to the tube coupling section 82. One end of a gas supply tube 21 that extends from the gas supply apparatus 30B is connected to the tube coupling section 82. Therefore, the air supplied from the gas supply apparatus 30B is supplied to the inside of the balloon 84 via the gas supply tube 21 and the gas supply hole of the over tube 80. The pressure inside the balloon 84 is detected by the first pressure sensor 81 and the detected pressure value is outputted to the manipulation state detection section 5b.

The manipulation state detection section 5b outputs manipulation situation data to a manipulation information acquiring section 6b of the system control apparatus 6. That is, the manipulation state detection section 5b detects whether the balloon 84 is in a predetermined swollen state or contracted state based on the pressure value detected by the first pressure sensor 81.

The manipulation state detection section 5b then determines the swollen state or contracted state from the detected value of the first pressure sensor 81 and outputs the detection result of the swollen state or contracted state to the manipulation information acquiring section 6b.

The gas supply apparatus 30B of the present embodiment is provided with a gas supply/exhaust section 33A that supplies air to the balloon 84 to change the balloon 84 from a contracted state to a swollen state or change the balloon 84 from a swollen state to a contracted state. The gas supply apparatus 30B is provided with a foot switch (not shown) so as to be able to select a gas supply state, exhaust state or stopped state as appropriate through the operation of the foot switch.

The mouth piece 90 is formed of elastic synthetic resin in a predetermined shape. The mouth piece 90 incorporates the second pressure sensor 91 that detects the patient's biting power applied to the mouth piece 90. The detected value of the second pressure sensor 91 is outputted to a biological information detection section 4b. The biological information detection section 4b outputs data indicating the biting power as a biological information detected value to a biological information acquiring section 6c of the system control apparatus 6.

Hardness control of the insertion portion when the insertion portion is inserted into a target region of the small intestine using the third medical system 10C configured as described above will be described.

First, when performing inspection or treatment using the endoscope, the operator registers the patient's biting power of the mouth piece 90 with a storage section 6d of the system control apparatus 6 as a threshold. Furthermore, the operator fits the mouth piece 90 at a predetermined position of the patient's oral cavity.

Next, the operator arranges the insertion portion 11H of the endoscope 1B in the insertion portion insertion hole 85 of the over tube 80 in a predetermined state and couples the gas supply tube 21 with the tube coupling section 82. The operator then drives the gas supply apparatus 30B, removes the air in the balloon 84 and changes the balloon 84 to a contracted state.

The operator then continues to insert the insertion portion 11H provided with the over tube 80 into the body via the mouth piece 90 attached to the patient's oral cavity. In this case, the operator performs an operation of bending the bending portion 11b or the like to cause the insertion portion 11 to reach the duodenum via the esophagus and the stomach. When the insertion portion 11 has passed through the duodenum, the operator starts insertion into the small intestine as shown in step S21 in FIG. 9.

Here, the operator operates the foot switch to supply air from the gas supply apparatus 30B. The balloon 84 is then swollen as shown in FIG. 10A, contacts the inner wall of the small intestine 100 under pressure and the distal end side portion 86 of the over tube 80 is fixed to the small intestine 100. In this state, the operator sets the hardness of the insertion portion 11H to 2 and performs manual operations such as operation of bending the bending portion 11b to cause a distal end portion 11a of the insertion portion 11H to move to the depth ahead of the over tube 80.

Next, as shown in FIG. 10B, the operator operates the bending knob 16 as appropriate to bend a bending portion 11b and causes the distal end portion 11a located at the depth to be in a holding state where it is hooked on the small intestine 100. Thus, the distal end portion 11a of the insertion portion 11H is fixed to the small intestine 100.

Next, the operator operates the foot switch to exhaust air in the balloon 84 and places the balloon 84 in a contracted state as shown in FIG. 10C. The operator then manually operates the over tube 80 to cause the over tube 80 to move forward along the insertion portion 11H set to hardness "2" as shown by a broken line.

After moving the over tube 80 forward, the operator operates the foot switch again to swell the balloon 84 and causes the distal end side portion 86 of the over tube 80 to be fixed to the small intestine 100. After that, the operator cancels the fixing of the distal end portion 11a to the small intestine 100, performs manual operation again to continue to move the distal end portion 11a of the insertion portion 11H forward. By repeating the aforementioned operations, the operator can insert the distal end portion 11a of the endoscope 1B into the depth of the small intestine 100.

During the insertion of the insertion portion 11H into the depth of the small intestine, the control section 6a is verifying whether or not the biting power exceeds a threshold as shown in step S22. As long as the comparison section 6e determines that the biting power does not exceed the threshold, the control section 6a assumes that the patient does not feel any pain and continues the insertion manipulation.

On the contrary, when a comparison section 6e determines that the biting power has exceeded the threshold, the control section 6a assumes that the patient may feel pain and moves to step S23. Here, the control section 6a verifies the current manipulation situation of the endoscope 1B and then controls the hardness of the insertion portion 11H.

That is, in step S23, the control section 6a verifies the detection result inputted from the manipulation information acquiring apparatus 5 to the manipulation information acquiring section 6b. Next, the control section 6a moves to step S24 and determines the manipulation situation from the verified determination result.

Here, upon verifying that a detection result that the balloon 84 is in a contracted state has been inputted to the manipulation information acquiring section 6b, the control section 6a determines the manipulation situation to be an insertion portion held state in which the distal end portion 11a is hooked on the wall of the small intestine, and outputs an instruction signal for changing the hardness of the insertion portion 11H to hardness 1 to the main control section 2b of the processor 2. This causes the motor 12m to be driven and causes the hardness of the insertion portion 11H to be changed to hardness 1.

Therefore, it is possible to alleviate pain of the patient while securing the hardness of the insertion portion 11H to a certain degree and enabling the over tube 80 to move forward.

On the other hand, in step S24, upon verifying that the detection result that the balloon 84 is in a swollen state has been inputted to the manipulation information acquiring section 6b, the control section 6a determines the manipulation situation to be an insertion portion inserted state and outputs an instruction signal for changing the hardness of the insertion portion 11H to hardness "0" to the main control section 2b of the processor 2. This causes the motor 12m to be driven and causes the hardness of the insertion portion 11H to be changed to hardness "0."

Therefore, it is possible to change the hardness of the insertion portion 11H from hardness "2" to hardness "0" and minimize the patient's pain due to the hardness of the insertion portion 11H. In this case, since the over tube 80 is fixed to the small intestine, though the hardness of the insertion portion 11H is "0," the insertion portion 11H can be moved forward along the over tube 80.

Thus, the control section of the system control apparatus can determine whether or not the patient feels pain due to the insertion manipulation of the insertion portion into the small intestine based on the determination result of the comparison section that compares the patient's power of biting the mouth piece during manipulation with a threshold.

When the comparison section determines that the patient feels pain, the control section determines the manipulation situation from the detection result inputted to the manipulation information acquiring section, automatically drives the motor of the hardness changing apparatus that adjusts the hardness of the insertion portion in a predetermined direction according to the manipulation situation, and can thereby alleviate the patient's pain.

Figure 11:
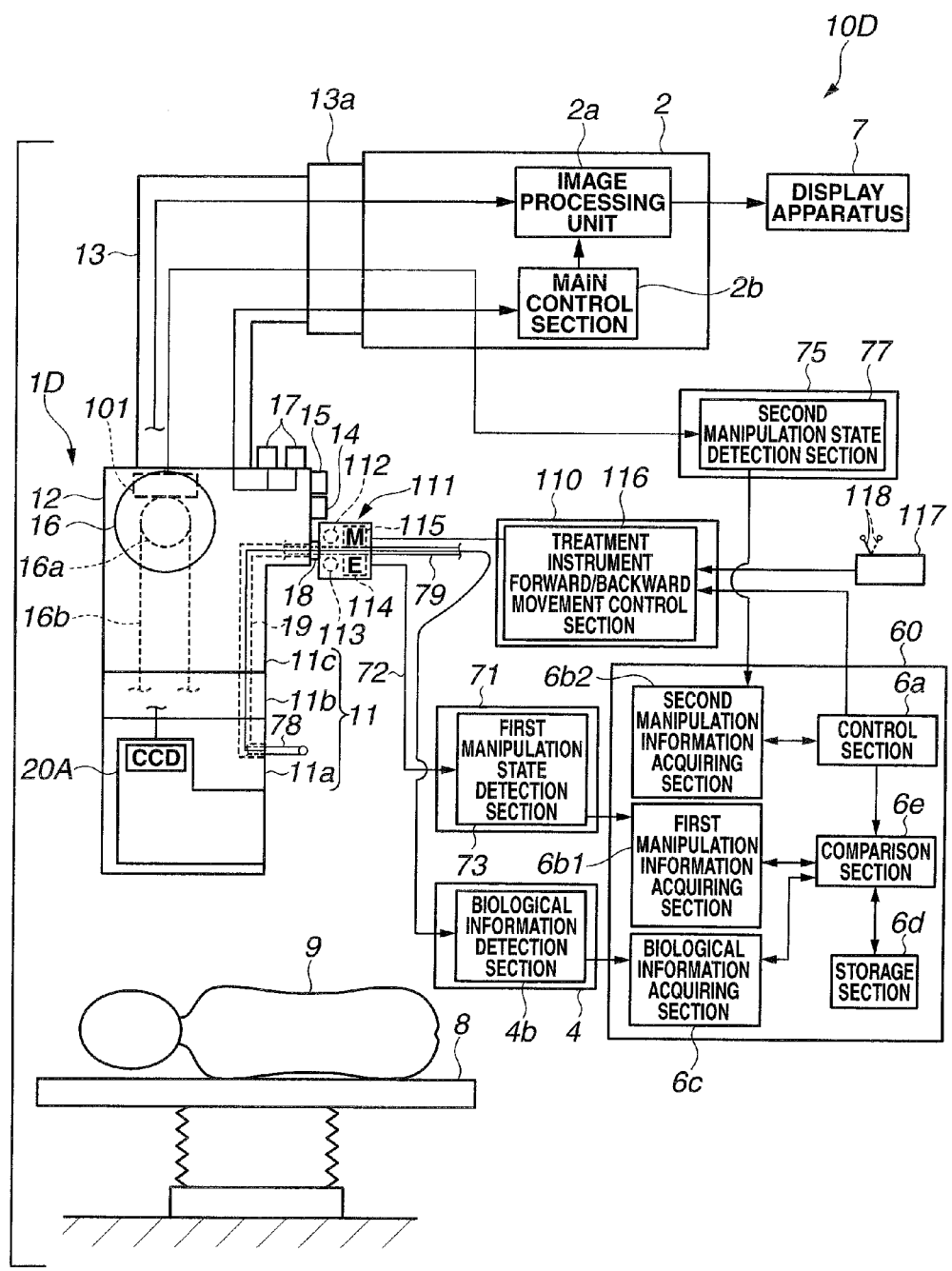
FIG. 11 and FIG. 12 are related to a fourth embodiment of a medical system.
Figure 12:
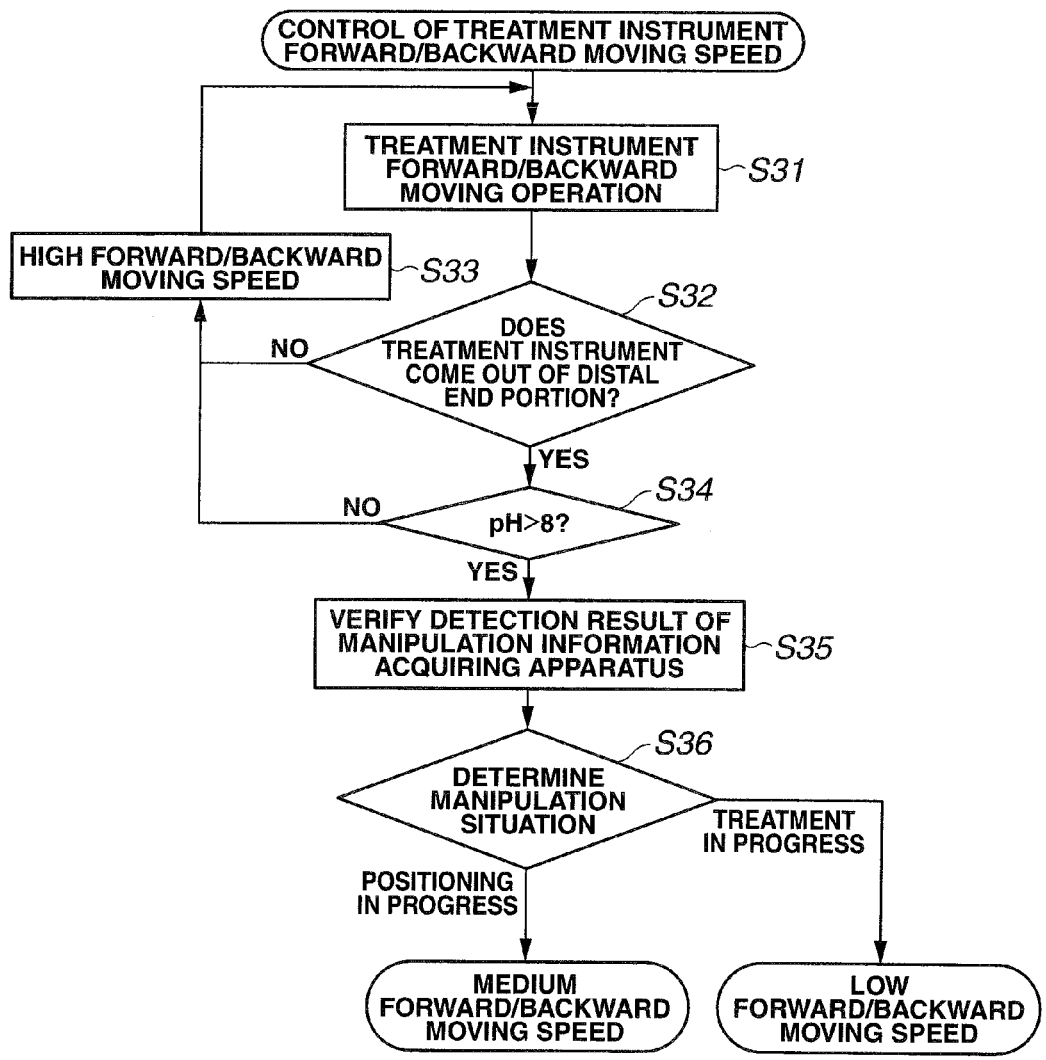

FIG. 11 and FIG. 12 are related to a fourth embodiment of a medical system, FIG. 11 is a diagram illustrating a configuration of a fourth medical system and FIG. 12 is a flowchart illustrating operation of the fourth medical system. In the present embodiment, members similar to those in the aforementioned embodiments will be assigned the same reference numerals and descriptions thereof will be omitted.

As shown in FIG. 11, the fourth medical system 10D is configured by including an endoscope 1D, a processor 2, a treatment instrument insertion portion electrically-driven operation forward/backward moving apparatus (hereinafter abbreviated as "electrically-driven forward/backward moving apparatus") 110 as the auxiliary device 3, a treatment instrument 79 moved forward/backward by the electrically-driven forward/backward moving apparatus 110, a bending portion operation detection apparatus 75, a treatment instrument operation detection apparatus 71 and a system control apparatus 60.

The endoscope 1D is a side-viewing endoscope having a side-viewing image pickup apparatus 20A and the operation section 12 is provided with a bending operation detection apparatus 101 as the manipulation information acquiring apparatus 5. The bending operation detection apparatus 101 is provided with an optical sensor that detects rotation of a bending knob 16 and detects whether or not a bending portion 11b is bent through the operation of the bending knob 16. When the bending knob 16 is operated to rotate, the bending operation detection apparatus 101 outputs a detection signal for notifying that the bending knob 16 is operated to rotate to a second manipulation state detection section 77 of the bending portion operation detection apparatus 75 which is the second manipulation information acquiring apparatus via the processor 2.

The second manipulation state detection section 77 of the bending portion operation detection apparatus 75 determines whether the state is a bending operation state in which the bending portion 11b is in operation through the operation of the bending knob 16 or a bending held state in which the bending portion 11b is held, from the number of times bending knob operation is performed and an amount of operation outputted per unit time and outputs the detection result of the bending operation state and the bending held state to a second manipulation information acquiring section 6b2.

The treatment instrument 79 is, for example, a contrast medium tube inserted into the bile duct and is provided with a pH sensor 78 at a distal end thereof. A signal line extending from the pH sensor 78 is outputted to a biological information detection section 4b. The biological information detection section 4b outputs a pH value to a biological information acquiring section 6c of the system control apparatus 60.

In the present embodiment, a control section 6a is configured to output an instruction signal for changing the forward/backward moving speed to a treatment instrument forward/backward movement control section 116 of the electrically-driven forward/backward moving apparatus 110.

The electrically-driven forward/backward moving apparatus 110 is provided with a body section 111 detachably attached to a treatment instrument insertion port 18. A pair of rollers 112 and 113, an encoder 114, a drive motor 115 and an operation switch 117 are provided in the body section 111.

The one roller 112 is fixed to a drive shaft (not shown) which is driven by the drive motor 115 to rotate clockwise or counterclockwise. The drive motor 115 is configured to be driven to rotate by a control signal generated based on an instruction signal inputted from the operation switch 117 to the treatment instrument forward/backward movement control section 116.

The other roller 113 is fixed to a driven shaft (not shown) and part of the driven shaft is arranged in the encoder 114. The encoder 114 is a sensor section provided for the treatment instrument operation detection apparatus 71 which is a first manipulation information acquiring apparatus. The encoder 114 can detect the rotation direction, the number of revolutions and the rotation speed of the driven shaft. The detected values are outputted to a first manipulation state detection section 73 via a signal line 72.

An insertion portion of the treatment instrument 79 is designed to be interposed under pressure between the rollers 112 and 113. When the drive shaft is rotated by the drive motor 115 with the insertion portion of the treatment instrument 79 interposed between the rollers 112 and 113, the treatment instrument 79 moves forward or backward as the drive shaft rotates. Such an electrically-driven forward/backward moving apparatus is described in detail in Japanese Patent Application Laid-Open Publication No. 2007-209750 or the like.

The operation switch 117 is provided with, for example, a tilting lever 118. The operation switch 117 is configured to output a control signal for moving the treatment instrument forward by setting the tilting direction of the tilting lever 118 to the forward direction as shown by a solid line and output a control signal for moving the treatment instrument backward by setting the tilting direction of the tilting lever 118 to the backward direction as shown by a broken line. Furthermore, the rotation speed of the drive motor 115 is made changeable, for example, in three stages; "high speed," "medium speed" and "low speed."

In the present embodiment, the "low speed" refers to a speed at which treatment can be performed in the bile duct using the treatment instrument. The "medium speed" is a speed that allows forward/backward movement without the treatment instrument damaging the bile duct. The "high speed" is an optimum speed until the treatment instrument approaches the duodenal papilla and a speed at which a tube member making up a treatment instrument channel 19 and a tubular body cavity wall are never damaged in the event of the treatment instrument contacting the tube member or the wall or the like.

On the other hand, the driven shaft is rotated as the drive shaft rotates and the amount of rotation thereof is detected by the encoder 114. The detection result of the encoder 114 of the present embodiment is designed to be outputted to the first manipulation state detection section 73 as an insertion amount notification signal for notifying the amount of insertion of the treatment instrument 79 inserted into the treatment instrument channel 19.

The forward/backward movement control of the electrically-driven forward/backward moving apparatus 110 when the contrast medium tube is inserted into the bile duct using the fourth medical system 10D configured as described above will be described.

First, when performing treatment using the endoscope, the operator registers a pH value of the patient's bile, for example, pH8 with a storage section 6d of the system control apparatus 60 as a threshold and also registers the channel length which is the length of the treatment instrument channel 19 in an insertion portion 11. Furthermore, the operator attaches the body section 111 of the electrically-driven forward/backward moving apparatus 110 to the treatment instrument insertion port 18.

Next, the operator starts inserting the insertion portion 11 into the body. An observation window of an image pickup apparatus 20 provided at a distal end portion 11a of the insertion portion 11 is placed face to face with the duodenal papilla.

Here, the operator arranges the treatment instrument 79 between the rollers 112 and 113 of the body section 111 of the electrically-driven forward/backward moving apparatus 110 to introduce the treatment instrument 79 into the body cavity and tilts the tilting lever 118 of the operation switch 117. The treatment instrument 79 then starts moving as shown in step S31 in FIG. 12. That is, the treatment instrument 79 moves inside the treatment instrument channel 19.

In step S32, the control section 6a verifies the comparison result of the comparison section 6e. That is, the control section 6a verifies whether or not the treatment instrument insertion amount data inputted to a first manipulation information acquiring section 6b1 exceeds a threshold (channel length) registered with the storage section 6d.

The control section 6a then sets the forward/backward moving speed of the treatment instrument 79 to a high speed as shown in step S33 to rotate drive motor 115 at a high speed while the treatment instrument insertion amount data inputted to the manipulation information acquiring section 6b1 is equal to or below the channel length, that is, until the amount of insertion is reached where the tip of the treatment instrument 79 comes out of the distal end portion 11a.

In step S32, upon determining that the treatment instrument insertion amount data inputted to the first manipulation information acquiring section 6b1 has exceeded a threshold registered with the storage section 6d, the control section 6a notifies that the treatment instrument has been led out into the body on the screen of the display apparatus 7 that the operator is observing. That is, characters such as "the treatment instrument will be led out" are displayed on the screen of the display apparatus 7 and the control section 6a moves to step S34. In this case, the treatment instrument is let out of the distal end portion 11a into the body at a high speed.

In step S34, the control section 6a verifies the determination result by the pH sensor 78. Here, the control section 6a sets the forward/backward moving speed of the treatment instrument 79 to a high speed as shown in step S33 during the interval that the pH value inputted to the biological information acquiring section 6c is equal to or below pH8.

Upon verifying that the inputted pH value is equal to or above pH8, the control section 6a moves to step S35. Here, the control section 6a verifies the current manipulation situation of the endoscope 1D and then controls the forward/backward moving speed of the treatment instrument 79.

That is, in step S35, the control section 6a verifies the detection result inputted from the bending portion operation detection apparatus 75 to the second manipulation information acquiring section 6b2. Next, the control section 6a moves to step S36 and determines the manipulation situation from the verified determination result.

Here, upon verifying that a detection result that a bending operation state has been inputted to the second manipulation information acquiring section 6b2, the control section 6a determines the manipulation situation to be positioning in progress. The control section 6a outputs an instruction signal for changing the rotation speed of the drive motor 115 to a "medium speed" to the treatment instrument forward/backward movement control section 116 based on this determination result. In this way, the forward/backward moving speed of the treatment instrument 79 is changed to the "medium speed."

On the other hand, upon verifying that a detection result of a bending held state has been inputted to the second manipulation information acquiring section 6b2, the control section 6a determines the manipulation situation to be treatment in progress. The control section 6a outputs an instruction signal for changing the rotation speed of the drive motor 115 to a "low speed" to the treatment instrument forward/backward movement control section 116 based on the determination result. In this way, the forward/backward moving speed of the treatment instrument 79 is changed to the "low speed."

Thus, the control section of the system control apparatus notifies the operator that the treatment instrument has been led out into the body, and then the control section automatically sets the rotation speed of the drive motor of the electrically-driven forward/backward moving apparatus to the "high speed" for the interval until the bile is verified by the pH sensor provided at the distal end of the treatment instrument. Thus, the treatment instrument can smoothly move through the insertion portion and the body.

On the other hand, when the bile is verified by the pH sensor, the control section determines whether the manipulation situation is positioning in progress or treatment in progress, and automatically sets the rotation speed of the drive motor of the electrically-driven forward/backward moving apparatus to the "medium speed" or "low speed" based on the determination result.

This allows the operator to operate the tilting lever of the operation switch without considering the forward/backward moving speed of the treatment instrument.

Figure 13:
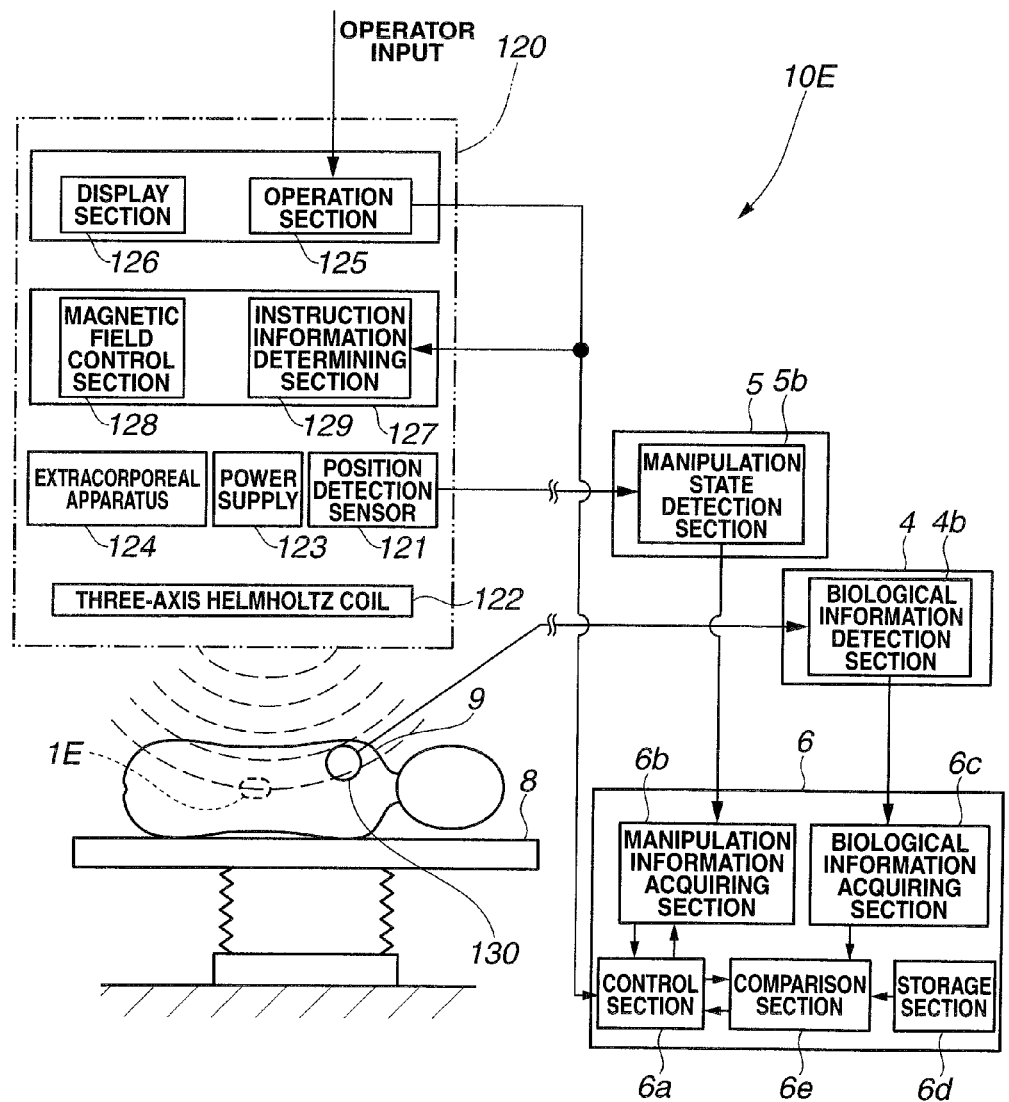
FIG. 13 and FIG. 14 are related to a fifth embodiment of a medical system.
Figure 14:
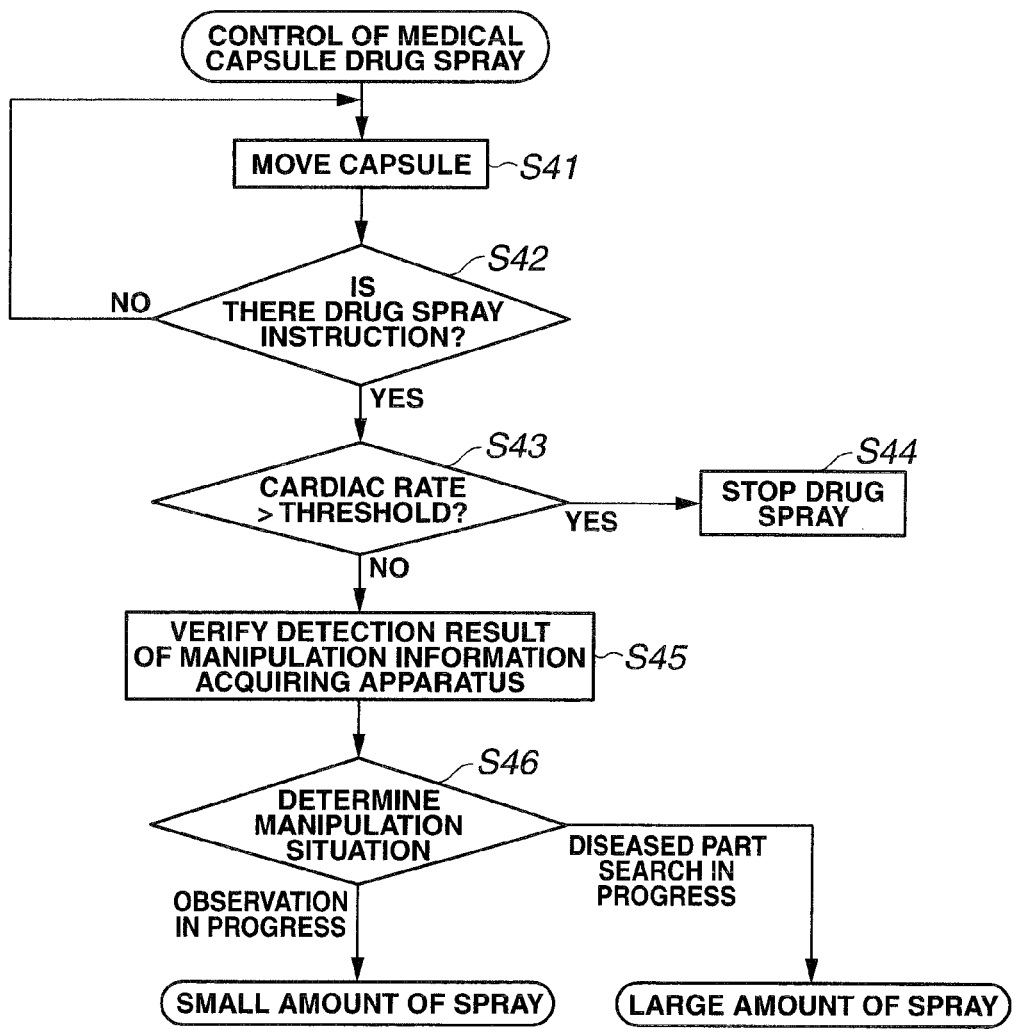

FIG. 13 and FIG. 14 are related to a fifth embodiment of a medical system, FIG. 13 is a diagram illustrating a configuration of a fifth medical system and FIG. 14 is a flowchart illustrating operation of the fifth medical system.

As shown in FIG. 13, a fifth medical system 10E is configured by including a capsule endoscope 1E, capsule endoscope control system 120 as the auxiliary device 3, a heart rate monitor 130 as the biological information acquiring apparatus 4 and a system control apparatus 6.

In the present embodiment, a control section 6a is configured to output an instruction signal for setting an amount of drug sprayed in an instruction information determining section 129 of the capsule endoscope control system 120, which will be described later.

The capsule endoscope control system 120 is configured by including a position detection sensor 121, a three-axis Helmholtz coil 122, a power supply 123, an extracorporeal apparatus 124, an operation section 125, a display section 126 and a system control section 127 or the like. The capsule endoscope 1E travels inside the body of the patient 9 based on the control of the capsule endoscope control system 120.

The position detection sensor 121 is the manipulation information acquiring apparatus 5 and detects position information and direction information of the capsule endoscope 1E. The three-axis Helmholtz coil 122 forms a magnetic field that acts on a permanent magnet incorporated in the capsule endoscope 1E. The power supply 123 supplies power to the three-axis Helmholtz coil 122. The extracorporeal apparatus 124 receives image information or the like transmitted from the capsule endoscope 1E. The operation section 125 receives control information directed to the capsule endoscope 1E from the outside such as the operator. The display section 126 displays image information or the like transmitted from the capsule endoscope 1E. The system control section 127 controls the power supply 123, the three-axis Helmholtz coil 122 or the display section 126 or the like.

The system control section 127 is provided with a magnetic field control section 128 and an instruction information determining section 129. The magnetic field control section 128 controls the direction of the magnetic field formed by the three-axis Helmholtz coil 122 based on the inputted control information or the like. The instruction information determining section 129 determines the instruction information.

The position detection sensor 121 detects guiding magnetism generated from the capsule endoscope 1E and outputs a signal based on the detected guiding magnetism to the system control section 127. In the present embodiment, the position detection sensor 121 also functions as a sensor section 5a of a manipulation information acquiring apparatus 5. That is, the detection result of the position detection sensor 121 is also outputted to a manipulation state detection section 5b. The manipulation state detection section 5b outputs manipulation situation data to a manipulation information acquiring section 6b of the system control apparatus 6.

That is, the manipulation state detection section 5b determines whether the capsule endoscope 1E is stopped for a large proportion of time within a predetermined time or is continuously changing for a large proportion of time, from the detection result of the position detection sensor 121 and outputs the detection result of stoppage or traveling to the manipulation information acquiring section 6b.

The power supply 123 is arranged so as to receive a control signal from the system control section 127 and supply power to the three-axis Helmholtz coil 122 based on the control signal. The extracorporeal apparatus 124 receives the image information acquired by the capsule endoscope 1E and transmitted to the outside and outputs the received image information to the system control section 127. Furthermore, the extracorporeal apparatus 124 also transmits an instruction determined by the instruction information determining section 129 to the capsule endoscope 1E. In the present embodiment, the extracorporeal apparatus 124 is enabled to transmit an instruction for spraying drug.

The capsule endoscope 1E accommodates various devices inside its outer enclosure. The outer enclosure includes an image pickup section, a guiding magnetism generation section that causes the three-axis Helmholtz coil 122 to generate guiding magnetism, a reservoir that stores drug, a drug release section that releases the drug stored in the reservoir, a control section that performs various types of control, a power supply section that supplies power to the image pickup section, the control section, the drug release section or the like and, for example, a permanent magnet.

Such a capsule endoscope is described in detail in, for example, Japanese Patent Application Laid-Open Publication No. 2005-102851 and Japanese Patent Application Laid-Open Publication No. 2006-263167.

The heart rate monitor 130 detects the patient's cardiac rate. The detected value of the heart rate monitor 130 is outputted to a biological information detection section 4b. The biological information detection section 4b outputs a cardiac rate to a biological information acquiring section 6c of the system control apparatus 6 as a biological information detected value.

Control of drug spray by the capsule endoscope 1E using the fifth medical system 10E configured as described above will be described.

First, when performing inspection or treatment using the endoscope, the operator registers the patient's cardiac rate with a storage section 6d of the system control apparatus 6 as a threshold. The operator then places the heart rate monitor 130 at a predetermined position of the patient 9 and instructs the patient to swallow the capsule endoscope 1E.

After that, the operator inputs an operation instruction to the operation section 125 and causes the capsule endoscope 1E to start to travel as shown in step S41. The operator observes an endoscope image displayed on the display section 126 and observes the presence/absence or the like of a lesion.

During the observation, the control section 6a enters a standby state waiting for an instruction for drug spray to be inputted to the operation section 125 as shown in step S42. In step 42, upon verifying an instruction of drug spray, the control section 6a moves to step 43 and verifies whether or not the cardiac rate of the patient 9 exceeds a threshold.

When the condition of the patient 9 is determined to be unstable in step 43, the control section 6a stops drug spray as shown in step S44. In this case, the control section 6a causes the display section 126 to display a comment "drug administration is dangerous" or the like. This allows the operator to continue, for example, an observation without performing drug administration.

On the other hand, when the patient 9 is determined to be stable in step 43, the control section 6a moves to step S45. Here, the control section 6a verifies whether the capsule endoscope 1E is stopped or traveling and sets an amount of spray.

Here, upon verifying that a detection result that the capsule 1E is in a stopped state has been inputted to the manipulation information acquiring section 6b, the control section 6a determines that the manipulation situation of the capsule endoscope 1E is observation in progress. The control section 6a outputs an instruction signal for setting the amount of spray to "small" to the instruction information determining section 129 of the system control section 127 to prevent an excessive amount of drug from being sprayed based on the determination result. This causes a predetermined amount of drug to be sprayed from the stopped capsule endoscope 1E.

On the other hand, upon verifying that a detection result that the capsule 1E is in a traveling state has been inputted to the manipulation information acquiring section 6b, the control section 6a determines that the manipulation situation of the capsule endoscope 1E is in search for the diseased part in progress. The control section 6a outputs an instruction signal for setting the amount of spray to "large" to the instruction information determining section 129 of the system control section 127 so that a predetermined amount of drug is sufficiently distributed to the diseased part based on the determination result. This causes the drug increased by a predetermined amount compared to the amount of spray "small" to be sprayed over the diseased part from the traveling capsule endoscope 1E.

Thus, upon verifying that an instruction for drug spray has been inputted to the control section of the endoscope control system, the control section of the system control apparatus determines whether the patient's condition is a condition appropriate for drug spray from the patient's cardiac rate, and can thereby stop or perform drug spray.

Furthermore, when performing drug spray, the control section verifies whether the capsule endoscope is in a traveling state or in a stopped state first and then changes and sets the amount of spray. This makes it possible to set the amount of drug sprayed over the lesion to a predetermined amount depending on whether the capsule endoscope is in a traveling state or in a stopped state.

The present invention is not limited only to the aforementioned embodiments, but can be modified in various ways without departing from the spirit and scope of the present invention.

What is claimed is:

1. A medical system comprising:
   an endoscope which is a first medical instrument;
   a gas supply apparatus which is a second medical instrument that supplies a gas to an insertion site at which an insertion portion of the endoscope is inserted;
   a biological information acquiring apparatus which is a biological information detection section that detects a blood flow rate at the insertion site as a biological information detected value;
   a manipulation information acquiring apparatus which is a manipulation information detection section that contacts the insertion portion of the endoscope and is combined with a roller that rotates as the insertion portion moves forward or backward to detect an amount of rotation of the roller as manipulation information; and
   a system control apparatus provided with a control section that outputs an instruction signal for changing an amount of gas supply to the gas supply apparatus based on a comparison result acquired by comparing the detected value detected by the biological information acquiring apparatus with blood flow rate data registered beforehand as a threshold, and a manipulation situation detected from the manipulation information detected by the manipulation information acquiring apparatus.

2. The medical system according to claim 1, wherein the manipulation information acquiring apparatus comprises a manipulation state detection section that determines, based on a detected value outputted from the detection section of the manipulation information acquiring apparatus within a predetermined time, whether a manipulation state is a state in which the insertion portion of the endoscope is inserted, inspection is performed by the endoscope or treatment is performed by the endoscope.

3. The medical system according to claim 1, wherein the control section corrects, when the determination result acquired by the manipulation information acquiring apparatus is a treatment state, a control value so that the proportion of reducing an amount of gas supply of the gas supply apparatus is smaller than the proportion of reducing an amount of gas supply when the determination result is an insertion state and an inspection state.

\* \* \* \* \*